(12) United States Patent
Toback et al.

(10) Patent No.: US 7,160,864 B2
(45) Date of Patent: Jan. 9, 2007

(54) METHODS FOR PRODUCTION OF GROWTH-PROMOTING PROTEINS AND PEPTIDES FOR KIDNEY EPITHELIAL CELLS

(75) Inventors: F. Gary Toback, Chicago, IL (US); Margaret M. Walsh-Reitz, River Forest, IL (US)

(73) Assignee: The University of Chicago, Chicago, IL (US)

( * ) Notice: Subject to any disclaimer, the term of this patent is extended or adjusted under 35 U.S.C. 154(b) by 146 days.

(21) Appl. No.: 10/892,617

(22) Filed: Jul. 16, 2004

(65) Prior Publication Data

US 2005/0095673 A1 May 5, 2005

Related U.S. Application Data

(62) Division of application No. 10/302,651, filed on Nov. 22, 2002, now abandoned.

(51) Int. Cl.
*A61K 38/00* (2006.01)
*A61K 38/04* (2006.01)
*C07K 14/00* (2006.01)
*C07K 16/00* (2006.01)
*C07K 17/00* (2006.01)

(52) U.S. Cl. .......................... 514/17; 514/13; 514/14; 514/15; 514/16; 530/300; 530/326; 530/327; 530/328; 530/329

(58) Field of Classification Search ..................... None
See application file for complete search history.

(56) References Cited

U.S. PATENT DOCUMENTS

| 5,135,856 | A | 8/1992 | Toback |
| 5,476,922 | A | 12/1995 | Toback |

OTHER PUBLICATIONS

Broccardo, M., et. al. (1975) "Relative Potency of Bombesin-Like Peptides" *Journal of Pharmacology* 55:221-227.
Coimbra, Terezil M. et. al. (1990) "Epidermal Growth Factor Accelerates Renal Repair in Mercuric Chloride Nephrotoxicity" *American Journal of Physiology* 259:F438-F443.
Hemibrock, David C., et. al. (1988) "Minimal Ligand Analysis of Gastrin Releasing Peptide. Receptor Binding and Mitogenesis" *Journal of Biological Chemistry* 263:7016-7019.
Joyce, Nancy, C., et. al. (1990) "In Vitro Pharmacologic Separation of Corneal Endothelial Migration and Spreading Responses" *Investigation Ophthalmology & Visual Science* 31,9:1816-1826.
Kartha, Sreedharan and Toback, F. Gary (1992) "Adenine Nucleotides Stimulate Migration in Wounded Cultures of Kidney Epithelial Cells" *Journal of Clinical Investigation* 90:288-292.
Kartha, Sreedharan, and Toback, F. Gary (1985) "Purine Nucleotides Stimulate DNA Synthesis in Kidney Epithelial Cells in Culture" *American Journal of Physiology* 249:F967-F972.
Levy, Elliot M., et. al. (1996) "The Effect of Acute Renal Failure on Mortality" *Journal of the American Medical Association* 275:1489-1494.
Medley, Susan R. and Toback, F. Gary (1989) "Autocrine and Paracrine Regulation of Kidney Epithelial Cell Growth" *Annual Review of Physiology* 51:33-50.
Miller, Steven B., et. al. (1994) "Hepatocyte Growth Factor accelerates Recovery From Acute Ischemic Renal Injury in Rats." *American Journal of Physiology* 266:F129-F134.
Mordan, Lawrence J. and Toback, F. Gary (1984) "Growth of Kidney Epithelial Cells in Culture: Evidence for Autocrine Control" *American Journal of Physiology* 246:C351-C354.
(1990) "The National Kidney and Urologic Diseases Advisory Board 1990 Long-Range Plan Window on the 21$^{st}$ Century" *U.S. Department of Health and Human Services*, NIH 90-583:12-13.
Rajagopal, Keshava, et. al. (1999). "RIBP, a Novel Rlk/Txk-and Itk-binding Adaptor Protein That Regulates T Cell Activation" *Journal of Experimental Medicine* 100:11, 1657-1668.
Segarini, Patricia R. et. al. (1987) "Membrane Binding Characteristics of Two Forms of Transforming Growth Factor-β" *The Journal of Biological Chemistry* 262:14655-14662.
Toback, F. Gary (1980) "Amino Acid Treatment of Acute Renal Failure" In Contemporary Issues in Nephrology, ed. Brenner, Barry M. and Stein, Jay H. vol. 6 pp. 202-228, Churchill Livingstone, New York.
Toback, F. Gary (1984) "Control of Renal Regeneration After Acute Tubular Necrosis" Nephrology, Proceedings IXth Internal Congress of Nephrology, ed. Robinson, Roscoe R. 1:748-762.

(Continued)

*Primary Examiner*—Olga N. Chernyshev
(74) *Attorney, Agent, or Firm*—Alice O. Martin; Barnes & Thornburg LLP

(57) ABSTRACT

Novel growth peptides derived from protein factors having molecular weights of about 22 and 45 kDa stimulate mitogenic activity of epithelial, but not fibroblastic cells, in particular, kidney epithelial cells. A source of the factors is scrape-wounded kidney epithelial cells in culture. Synthetic peptides having sixteen amino acids or less, in particular a hexapeptide, YPQGNH (SEQ ID NO: 2) maintain the mitogenic activity. The peptide AQPYPQGNHEASYG (14-Ser) (SEQ ID NO: 15) is effective in reversing acute renal failure in animals. The growth-promoting characteristics of the 22 and 45 kDa proteins and the peptides are useful in treating and diagnosing patients with kidney disease. Nucleotide sequences that encode the factor are useful to develop probes to locate similar factors, to identify genetic disorders involving the factor, and to produce the factor by genetic recombinant methods. The nucleotide sequences and fragments thereof, are also useful for diagnosis and treatment of kidney disorders.

4 Claims, 2 Drawing Sheets

OTHER PUBLICATIONS

Toback, F. Gary (1980) "Induction of Growth in Kidney Epithelial Cells in Culture by Na+" *Proceedings of the National Academy of Sciences*, USA 77:6654-6656.

Toback, R. Gary (1992) "Regeneration After Acute Tubular Necrosis" *Kidney International* 41:226-246.

Toback, F. Gary, et. al. (1984) "Stimulation of DNA Synthesis in Kidney Epithelial Cells in Culture by Potassium" *American Journal of Physiology* 247:C14-C19.

Walsh-Reitz, Margaret M., et. al. (1986) "Lowering Extracellular Na+ Concentration Releases Autocrine Growth Factors From Renal Epithelial Cells" *Proceedings of the National Academy of Sciences USA* 83:4765-4768.

Walsh-Reitz, Margaret M. and Toback, F. Gary (1983) "Vasopressin Stimulates Growth of Renal Epithelial Cells in Culture" *American Journal of Physiology* 245:C365-C370.

METHODS FOR PRODUCTION OF GROWTH-PROMOTING PROTEINS AND PEPTIDES FOR KIDNEY EPITHELIAL CELLS

This application is a divisional application of U.S. Ser. No. 10/302,651 filed Nov. 22, 2002 now abandoned, which claims priority to U.S. Ser. No. 08/974,775 filed Nov. 20, 1997, now U.S. Pat. No. 6,096,706 issued Aug. 1, 2002 and U.S. Ser. No. 09/590,864, filed Jun. 9, 2000, now U.S. Pat. No. 6,534,290 issued Mar. 18, 2003.

The United States government may have rights in the disclosed invention because of partial support under National Institutes of Health #DK 39689.

Novel growth peptides derived from protein factors having molecular weights of about 22 and 45 kDa stimulate mitogenic activity of epithelial, but not fibroblastic cells, in particular, kidney epithelial cells.

Acute renal failure is a serious disease associated with high mortality for which no "real" treatment currently exists. Acute renal failure is defined as the abrupt disruption of previously normal kidney function. It is caused by a wide variety of mechanisms including circulatory failure (shock), vascular blockade, glomerulonephritis, and obstruction to urine flow. In addition it can occur following surgery, trauma, sepsis, or with certain medications, particularly antibiotics and anticancer agents.

In 1985 some 140,000 Americans were hospitalized with acute renal failure (see 1990 Long Range Plan). The average cost of treatment associated with these cases was over $9000. Based on the growth in the disease over the past several years and normal inflation, it was estimated that currently some 240,000 patients develop acute renal failure annually at a cost of over $10,000 per patient. That translated to a staggering total cost to the U.S. healthcare system of almost $2.5 billion per year.

TABLE 1

Average Cost Per Hospital Discharge for Kidney and Urologic Disease, United States, 1985[1]

| | Number of Discharges | Average Cost per Discharge |
|---|---|---|
| 1. Acute renal failure | 139,134 | $9,329 |
| 2. Chronic renal failure | 395,066 | 9,249 |
| 3. Kidney disease of diabetes mellitus | 96,731 | 6,819 |
| 4. Kidney cancer | 47,384 | 6,145 |
| 5. Hypertensive renal disease | 182,625 | 5,796 |
| 6. Other intrinsic/systemic diseases | 79,683 | 5,061 |
| 7. Bladder Cancer | 125,108 | 4,758 |
| 8. Impotence | 30,452 | 4,344 |
| 9. Prostate Cancer | 246,201 | 3,791 |
| 10. Testicular Cancer | 14,219 | 3,711 |
| 11. Benign prostatic hyperplasia | 482,348 | 3,648 |
| 12. Polycystic kidney disease | 44,155 | 3,213 |
| 13. Glomerulonephritis | 79,531 | 3,135 |
| 14. Bladder disorders | 342,211 | 3,064 |
| 15. Urinary stone disease | 453,018 | 2,920 |
| 16. Urinary tract infection | 1,583,309 | 2,549 |
| 17. Incontinence | 162,574 | 2,547 |
| 18. Hematuria | 173,495 | 2,375 |
| 19. Prostatitis | 108,024 | 2,010 |
| 20. Obstructive uropathy[2] | 397,074 | 1,842 |
| 21. Other genitourinary infections | 147,215 | 1,339 |
| 22. Preeclampsia | 139,000 | 1,025 |
| 23. Testicular dysfunction | 7,019 | 950 |

[1]Includes payments to physicians.
[2]Includes vesicoureteral reflux.
Sources: National Center for Health Statistics: National Hospital Discharge Survey, 1985 (all listed diagnoses). Department of Veterans Affairs, for year ending September 30, 1986 (first-listed diagnoses) (unpublished). Health Care Financing Administration, Medicare provider analyses and review data, 1985 (unpublished).

As can be seen in Table 1 from the Plan, kidney disease contributes to major medical costs in the United States, so factors reducing time to recovery, are beneficial to society.

Equally significant, is the fact that the number of cases of acute renal failure is growing at a rate of 9% per year (NIH, 1995) and this high rate of growth is expected to continue. A reason given for this rise in the incidence of renal failure is that "sicker" patients with a high risk of renal failure are surviving longer.

1. Older Patients, who have significantly higher incidence of acute renal failure (e.g., patients over 65 are 5 times more likely to be hospitalized for acute renal failure than those ages 45 to 64) are now surviving serious medical incidents (e.g., heart attack, stroke) as well as complicated surgery. Improved hospital intensive care units with more sophisticated monitoring and life support systems also aid in keeping "sicker" patients alive. In addition improved therapeutic agents for treating cancer and life-threatening infections are often nephrotoxic.

2. Nenoates, who have an extremely high risk of kidney failure are also surviving at shorter terms and at significantly lower birth weights. Such infants formerly had difficulties overcoming sever lung and heart problems, but these problems can now be successfully treated with improved drugs and techniques, particularly in specialized neonatal intensive care units.

Because these advances in treatment modalities are expected to continue and even accelerate, it is likely that the number of cases of acute renal failure will continue to increase, perhaps at an even faster rate.

At the present time no real "cure" exists for acute renal failure. The current method of treatment is to "rest" the kidney by performing dialysis to correct metabolic imbalances and wait for kidney function to return spontaneously.

Dialysis is a technique in which impurities and toxins from the blood, that are normally cleared through the kidneys are artificially removed through an extra-corporeal circuit and filter (hemodialysis) or through the peritoneal membrane. By removing such impurities the life threatening metabolic imbalances resulting from kidney failure can be corrected and the patient stabilized.

Mortality rates resulting from a patient's developing acute renal failure are extremely high. A recent study (Levy et al., 1996) that analyzed the effect of acute renal failure on patient mortality cites such rates as ranging from 42% to 88% based on 18 previously published reports. These rates have remained essentially unchanged since the early 1950's. In the 1996 study itself the mortality rate for hospitalized patients who developed acute renal failure was 5 times higher compared to similar patients without renal failure (34% vs. 7%).

A key finding of this study is that "acute renal failure appears to increase the risk of developing sever non-renal complications that lead to death and should not be regarded as a treatable complication of serious illness." Thus it appears that the rapid reversal of acute renal failure can significantly reduce the risk of mortality in patients who also frequently have complicated clinical courses by preventing the development of sever and often fatal non-renal complications.

It has long been known that the kidney is one of the few human organs that has an ability to repair itself after injury. Even in cases where the kidney has been irreversibly damaged, and there is extensive necrosis of kidney cells, strong evidence exists that some new cell growth occurs.

It has been proposed that growth factors are a therapeutic approach to stimulate or augment the regenerative process in the injured kidney and thereby reduce the severity and shorten the course of acute renal failure. The use of growth factors as a treatment for acute renal failure was first proposed by Toback (1984). However, finding suitable growth factors proved difficult. The rationale for this strategy was subsequently expanded after several specific growth factor proteins were identified (Mendley and Toback, 1989; Toback 1992 a and b). However, no factors have yet been confirmed as useful in treating humans.

Growth factors acting in vivo to stimulate proliferation and migration of noninjured tubular cells in the kidney, and possibly to facilitate recovery of sublethally-injured cells as well, would be beneficial. A specific growth factor could be used in combination with sufficient nutrients, calories, and dialytic therapy to increase survival of patients with renal problems. For example, administration of growth factors could (1) increase positive outcomes in patients with cadaveris renal transplants, a situation in which acute renal failure is associated with increased rejection, (2) shorten the duration of acute renal failure which would increase patient survival, and (3) reduce the number of days required for hemodialysis treatment during the renal failure syndrome.

Autocrine growth factors are produced locally by the same cells on which they act. They appear to be produced in response to a stimulating even such as cell injury. Moreover, they are produced in extremely small quantities and may exist at detectable levels for only a short time. Consequently, they have been quite difficult to isolate and identify.

Two other types of growth factors—paracrine and endocrine—both appear to have some role in stimulating kidney cell growth. Paracrine factors act on adjacent cells (rather than on themselves) while endocrine factors are produced in one cell and transported (e.g., by the blood stream) to act on another, distant cell. Several of these types of factors, which are typically produced in larger quantities, and have a longer "half life" than some autocrine factors, have been discovered, and their cDNAs identified.

Animal and Clinical Studies

Several growth factors have been studied in an acute renal failure rat model to determine their efficacy in speeding recovery. The results of these studies give encouraging support to the theory that growth factors may play a major role in accelerating kidney repair. Three of the most important of these are:

1. Epidermal growth factor (EGF) The EGF factor has been reported to accelerate recovery in rats with acute renal failure. However, it was noted that EGF also mobilizes calcium from bone, which is a serious side effect that will likely prohibit its use in humans.

2. Insulin like growth factor-1 (IGF-1) Several studies in the rat model confirm that this factor is indeed efficacious. However, in two clinical studies in humans IGF-1 did not appear to have any substantial effect in speeding a patient's recovery from acute renal failure.

3. Osteogenic protein-1 (OP-1) is a bone growth factor already approved for human use in repairing bone, cartilage, and eye tissue. Although OP-1 may play a key role in the embryonic development of human kidneys, it is not clear how it works to help repair adult kidney cells. It is possible that OP-1 and other autocrine kidney growth factors together could have complementary mechanisms of action.

Autocrine Kidney Growth Factors

Although the animal study results on the previously identified growth factors are encouraging, none of these factors are used clinically at present. Of particular note is that the kidney messenger RNA for the three growth factors described above—EGF, IGF-1 and OP-1—actually decreases in the kidneys during acute renal failure. Logically, if a growth factor is to be effective in repairing injury and reversing acute renal failure, its levels would be expected to increase during this clinical event.

Some of the factors already identified are released by kidney epithelial cells and are capable of stimulating growth of the cells in an autocrine manner. For example, monkey kidney (BSC-1) cells respond to culture medium with a reduced concentration of potassium by releasing the "Low Potassium Growth Factor," and respond to a reduced concentration of sodium by releasing the "Low Sodium Growth Factor" (Mordan and Toback, 1984; Walsh-Reitz et al., 1986; Toback et al. 1992b and 1995).

A significant need exists for new therapeutic approaches to "cure," or at a minimum, speed the reversal of acute renal failure.

SUMMARY OF THE INVENTION

This invention is directed to growth promoting proteins and peptides, initially referred to as a protein Wound Growth Factor (WGF) because of the manner of production in culture of the basic factor. Further analysis revealed factors of two molecular weights,

```
                        1              12      16
22 kDa isoform:  NH2-AQPYPQGNHEA T    S SSF-COOH  (SEQ ID NO: 4)

1              12    14
45 kDa isoform:  NH2-AQPYPQGNHEX A/S  Y  G-COOH    (SEQ ID NO: 1)
```

Peptides of various lengths are within the scope of the present invention, as long as the mitogenic hexamer sequence, NH$_2$-tyrosine-proline-glutamine-glycine-asparagine-histidine-COOH (YPQGNH) (SEQ ID NO: 2) is included.

An embodiment of a novel peptide is a potent mitogen for monkey kidney epithelial cells in culture 14 amino acids, AQPYPQGNHEASYG (14-Ser) (SEQ ID NO: 15). Compared to other known renal growth factor mitogens, this peptide has a mitogenic effect that is either additive with, equivalent to, or more potent than other known factors: e.g., epidermal growth factor, acidic fibroblast growth factor, basic fibroblast growth factor, insulin-like growth factor, vasopressin, or calf serum.

The native factor (WGF) is released into culture medium when a kidney cell monolayer is subjected to mechanical scrape wounding with a pipette tip. This was a novel finding. That is, the growth factor is released from scrape wounded kidney cells and can stimulate proliferation of the cells. Thus, it is an autocrine growth factor. A source of cells which releases the factor is the BSC-1 cell line (nontransformed African green monkey kidney epithelial cells). (ATCC CCL 26 8S-C-1) "Bioactive WGF" is defined herein as a factor that stimulates mitogenic activity in cultured renal cells and is generally what is meant by "WGF" herein. "WGF" includes several peptides with mitogenic activity. These peptides may be synthesized by techniques well known to those of skill in the art, including recombinant genetic technology. A preferred peptide has 14 amino acids, the sequence is AQPYPQGNHEASYG (14-Ser) (SEQ ID NO: 15).

The appearance of growth-promoting activity after wounding seems to be mediated by the proteolytic activation of an inactive precursor of WGF. Evidence for this is that preincubation of the cells for 10 minutes with each of the following diverse protease inhibitors prevented the appearance of growth-promoting activity after wounding: aprotinin, phenylmethylsulfonyl-fluoride (Sigma) (PMSF), antipain, L-1-chloro-3-(4-tosylamido)-7-amino-2-heptanone-hydrochloride (TLCK) or α$_2$-macroglobulin. None of these agents inhibited cell growth when added to cells of non-wounded cultures. When added to the medium after the appearance of WGF mitogenic activity, neither PMSF nor aprotinin appeared to inhibit the increment in cell proliferation. HPLC-purified WGF does not appear to be a protease because it did not exhibit proteolytic activity when assayed using Protease Substrate Gel tablets (BioRad).

WGF exhibits a growth-promoting activity that is released into the culture medium of BSC-1 cells. Isolation and purification of components responsible for this growth-promoting activity reveals that it behaves on sodium dodecylsulfate (SDS)-polyacrylamide electrophoresis as if it has a relative molecular mass (M$_r$) of 22 and/or 45 kilodaltons (kDa). WGF is a protein that is a mitogen for monkey kidney BSC-1 cells, but not for 3T3 fibroblasts. Release of WGF also appears to be relatively kidney epithelial cell-type specific in origin because it appears after wounding BSC-1 cells in culture, but not after wounding fibroblasts in culture.

Therefore, an aspect of the present invention is a protein designated "WGF" having the following characteristics:
  a) an estimated molecular weight of about 45 and/or 22 kDa, said estimate obtained by electrophoresing the HPLC-purified protein on an SDS-polyacrylamide gel;
  b) capability of stimulating mitogenic activity when in contact with cultured cells; and
  c) released by BSC-1 cells in culture by scrape wounding.

In particular, the protein has a partial amino acid sequence at its amino terminal end as follows: NH$_2$-alanine-glutamine-proline-tyrosine-proline-glutamine-glycine-asparagine-histidine-glutamic acid-X-alanine/serine-tyrosine-glycine-COOH (SEQ ID NO: 1). (X=undefined amino acid).

Another WGF protein has an estimated molecular weight of about 22 kDa, said estimate obtained by electrophoresing the HPLC-purified protein on an SDS-polyacrylamide gel and a partial amino acid sequence at its amino terminal end as follows: NH$_2$-alanine-glutamine-proline-tyrosine-proline-glutamine-glycine-asparagine-histidine-glutamic acid-alanine-threonine-serine-serine-serine-phenylalinine-COOH (SEQ ID NO: 4).

A protocol suitable to purify WGF from conditioned cell culture medium utilizes ultrafiltration, heparin-affinity chromatography and reversed-phase (RP) high-performance liquid chromatography (HPLC). 6,400 fold purification is achieved, although the yield of WGF protein is extremely low, usually in the range of 50 ng protein per liter of conditioned medium.

The size of bioactive WGF was defined by electrophoresing HPLC-purified WGF on SDS gels in parallel with standard proteins (i.e., proteins of known sizes), slicing the gel into 2-mm wide gel fragments, eluting each fragment in buffer, and the assaying the eluate for mitogenic activity using cultures of BSC-1 cells. This experimental strategy indicated that WGF proteins have an estimated M$_r$ of 22 and 45 kDa and are mitogenic.

Generally "proteins" is the term used for molecules of about 50 amino acids or greater. Peptides are smaller.

A single sharp peak of absorbing material at 214 nm obtained by RP-HPLC exhibits growth-promoting activity on kidney epithelial but not fibroblastic cells, and yields several bands on SDS-polyacrylamide gel electrophoresis following silver staining.

Amino acid compositional analysis of material that formed the sharp peak confirmed the protein character of WGF. Microsequencing revealed the first 16 amino acids of the amino (NH$_2$) terminus of the 22 kDa isoform: NH$_2$-alanine-glutamine-proline-tyrosine-proline-glutamine-glycine-asparagine-histidine-glutamic acid-alanine-theronine-serine-serine-serine-phenylalanine-COOH (SEQ ID NO: 4). For the 45 kDa isoform 14 amino acids at the amino-terminus have been identified: NH$_2$-alanine-glutamine-proline-tyrosine-proline-glutamine-glycine-asparagine-histidine-glutamic acid-X-alanine/serine-tyrosine-glycine-COOH (SEQ ID NO: 1). The identity of the amino acid at position 11 is uncertain (X), and it is not possible to determine whether an alanine (A) or serine (S) is at position 12. A search of the seven peptide sequence databases in the Experimental GENINFO(R) BLAST Network Service (Blaster) operated by the National Center for Biotechnology Information (NCBI) indicated that the amino-terminal sequences are that of novel proteins.

Of substantial importance is the additional finding that peptides smaller than the full preferred 16 amino acid sequence also have strong mitogenic specific activity. This finding is quite significant because these small peptide (1) are much less likely to be antigenic (i.e., they can be directly infused into another animal or human without being rejected by the immune system) and (2) can be readily prepared in large quantities and modified using a peptide synthesizer without first having to find a cDNA clone that encodes the entire 22 or 45 kilodalton protein, and then expresses the recombinant protein.

In addition to producing the factor by wounding cultured cells, synthetic peptides are produced that contain the mitogenic activity. Of particular interest is that a synthetic peptide whose sequence is based on the first eleven amino acid residues of the 22 kDa protein exhibits mitogenic activity. Moreover, other polypeptides that are short peptide domains of the factor are also within the scope of the present invention. An hexamer was the smallest peptide which still maintained mitogenic activity (YPQGNH) (SEQ ID NO: 2).

A peptide comprising an amino acid sequence of NH$_2$-tyrosine-proline-glutamine-glycine-asparagine-histidine-COOH (SEQ ID NO: 2) is suitable for the practice of the invention. Generally, the peptide has a length of from 7 to 16 amino acids but other lengths are also suitable if the mitogenic and/or antigenic function is preserved.

Both transforming growth factor-beta 2, and a synthetic 5-amino acid peptide having the sequence YPQGN (SEQ ID NO: 3) block the mitogenic effect of AQPYPQGNHEASYG (SEQ ID NO: 15). The glycosaminoglycans, heparin and keratan sulfate, each potentaiate the mitogenic effect of the peptide.

A peptide having the sequence AQPYPQGNHEASYG (SEQ ID NO: 15) and other related peptides derived from the NH$_2$-termini of Wound Growth Factor isoforms, were evaluated for their capacity to alter the course of acute renal failure (ARF) in a nephrotoxic rat model; this syndrome commonly afflicts humans.

Mercuric chloride given subcutaneously (s.c) was used to induce ARF in rats, and a solution of each peptide was evaluated for its capacity to enhance survival and speed recovery of renal function, assessed by measuring the serum creatinine concentration during the ensuing 7 days.

Administration of a peptide having the sequence AQPYPQGNHEASYG (SEQ ID NO: 15), s.c. 1 hour after administration of mercuric chloride significantly improved recovery of renal function two days later and improved survival after three days. Similar beneficial effects of the peptide on survival and recovery of renal function were observed when it was administered 24 hours before induction of the ARF syndrome.

Evidence that the peptide improved survival and recovery of renal function by stimulating DNA synthesis in cells near the site of mercuric chloride-induced renal injury was obtained by using bromodeozyuridine to label DNA in the regenerating kidneys. The peptide was more potent than epidermal growth factor, an agent of known efficacy in this model system, in promoting survival when given 24 hours before renal injury, and equivalent when given shortly thereafter. Improved survival and a more rapid recovery of renal function in response to treatment with the peptide are expected in humans with nephrotoxic as well as ischemic ARF.

Suitable peptides for the practice of the invention include:

| | |
|---|---|
| AQPYPQGNHEATSSSF; | (SEQ ID NO: 4) |
| AQPYPQGNHEATSSS | (SEQ ID NO: 5) |
| AQPYPQGNHEA | (SEQ ID NO: 6) |
| AQPYPQGNHEAT; | (SEQ ID NO: 7) |
| AQPYPQGNHEATS; | (SEQ ID NO: 8) |
| AQPYPQGNHEATSS; | (SEQ ID NO: 9) |
| AQPYPQGNHEATSY; | (SEQ ID NO: 10) |
| AQPYPQGNHEAAYG; | (SEQ ID NO: 11) |
| AQPYPQGNHEAAY; | (SEQ ID NO: 12) |
| AQPYPQGNHEAA; | (SEQ ID NO: 13) |
| AQPYPQGNHE; | (SEQ ID NO: 14) |
| AQPYPQGNHEASYG; | (SEQ ID NO: 15) |
| AQPYPQGNHEASY; | (SEQ ID NO: 16) |
| AQPYPQGNHEAS; | (SEQ ID NO: 17) |
| QPYPQGNHEA; | (SEQ ID NO: 18) |
| AQPYPQGNH; | (SEQ ID NO: 19) |
| QPYPQGNHE; | (SEQ ID NO: 20) |
| PYPQGNHEA; | (SEQ ID NO: 21) |
| QPYPQGNH; | (SEQ ID NO: 22) |
| PYPQGNHE; | (SEQ ID NO: 23) |
| YPQGNHEA; | (SEQ ID NO: 24) |
| PYPQGNH; and | (SEQ ID NO: 25) |
| YPQGNHE; | (SEQ ID NO: 26) |
| YPQGNHEATSSSF; | (SEQ ID NO: 27) |
| YPQGNHEATSSS; | (SEQ ID NO: 28) |
| YPQGNHEATSS; | (SEQ ID NO: 29) |
| YPQGNHEATS; and | (SEQ ID NO: 30) |
| YPQGNHEAT. | (SEQ ID NO: 31) |

A mitogenic fragment of protein is the peptide YPQGNH (SEQ ID NO: 2); a peptide having the sequence AQPYPQGNHEASYG (SEQ ID NO: 15) is preferred.

A composition comprising the proteins or peptides described herein is within the scope of the invention.

A method for producing a protein or peptide of the present invention includes the steps of:
  a) culturing kidney epithelial cells in media,
  b) wounding the cells in culture, and
  c) obtaining the protein from the conditioned media.

The protein obtained is isolated from the conditioned media and purified. A source of the kidney epithelial cells in culture is the BSC-1 African green monkey kidney epithelial cell line.

A recombinant DNA method of making a protein or peptide of the present invention includes the following steps:
  a) obtaining a nucleotide sequence encoding the protein or peptide; and
  b) using the nucleotide sequence in a genetic expression system to make the protein or peptide.

The peptide can also be prepared directly on a peptide synthesizer without recourse to cellular or molecular biological techniques.

An antibody to WGF is an aspect of the present invention. Availability of the antibody provides a diagnostic tool to measure the amount of the factor in urine, blood and tissue. New diagnostic insights are facilitated in patients receiving drugs with nephrotoxic potential during treatment of infections or malignancies, and in individuals with renal injury or neoplasia. Such an antibody may also be used to detect renal cancer in the remnant kidneys of patients undergoing chronic peritoneal and hemodialysis. The antibody is directed to a protein or peptide including the active site, that is, generally includes YPQGHN (SEQ ID NO: 2).

A diagnostic kit is used to measure the quantity of a WGF protein or a mitogenic peptide therefrom, in a biological sample to detect acute renal injury or the early onset of kidney disease, monitor treatment of renal cell cancer, or recognize the conversion of benign renal cysts in chronic dialysis patients to carcinomas or cystadenocarcinomas. The kit includes in separate containers:

a) an antibody to WGF or to a mitogenic peptide therefrom; and b) a means for detecting a specific complex between the WGF protein or a mitogenic peptide and the antibody.

The invention includes the use of the protein in preparing a composition for medical treatment of kidney disease, said preparation comprising obtaining the protein and adding to it a suitable carrier.

The new kidney growth factor proteins and peptides of the present invention and antibodies directed to them have diverse uses in clinical medicine. The WGF peptides are useful for stimulating kidney cell growth, a characteristic useful for treatment of acute renal failure. It is particularly desirable to speed recovery in patients with acute renal failure, especially those receiving cadaveric kidney transplants. Infusion of the protein into patients is directed to shortening the duration of the acute renal failure episode which would increase patient survival, and reduce the number of days required for hemodialysis treatment during the renal failure syndrome. The peptides also provide an in vitro standard of comparison for other candidate growth factors.

It is expected that WGF will have a role as a therapeutic agent to slow the progression of established kidney disease such as chronic glomerulonephritis or interstitial nephritis. WGF and its receptor appears to be on the surface of renal epithelial cells. If WGF is found to be a ligand for receptors on the surface of specific renal epithelial cell types along the nephron, it is to be considered in cancer chemotherapy. If it is found to be cancer cell-type specific, the growth factor could be conjugated with a cellular toxin, a radioactive isotope, or cytotoxic antibody to produce powerful new chemotherapeutic agents.

A method of treating a person with acute renal failure, includes: a) preparing a pharmacologically effective amount of native WGF protein or WGF-derived peptide in a suitable diluent; and b) administering the preparation to the person. The WGF may be ligated to a cytolytic ligand, e.g. a toxin.

The invention also relates the use of a protein or peptide described herein to obtain a composition useful in treating a person with acute renal failure.

DETAILED DESCRIPTION OF THE INVENTION

Production of the Wound Growth Factor

Figure 1:
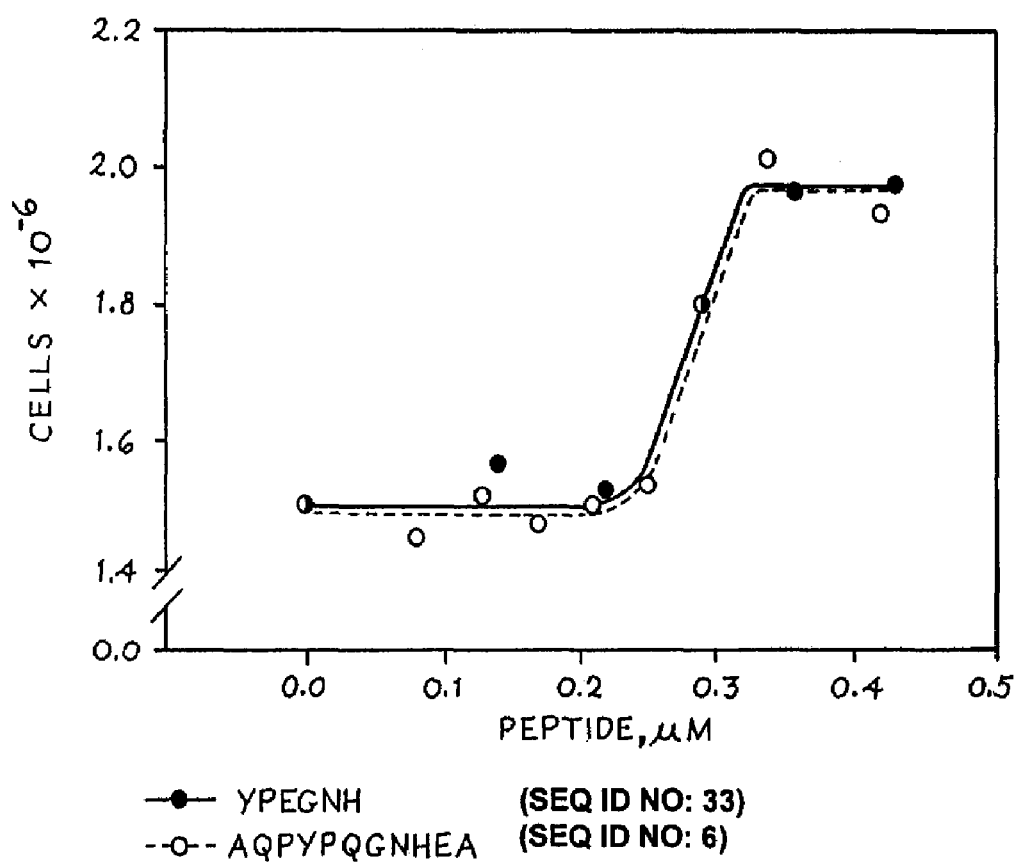
FIG. 1 illustrates growth-promoting activity of wound growth factor-derived peptides on growth of BSC-1 cells.

Confluent monolayer cultures were mechanically scraped using a 200 μL pipet tip (Continental Laboratory Products, San Diego, Calif.). When observed under a microscope, this scraping did not appear to damage the cells, only to cause them to separate from each other and retract, leaving a narrow path in the culture dish that could be seen with the naked eye. (This process of scraping the cells has been termed "wounding" and has been used for many years as a model system to study repair of corneal abrasions of the eye. In effect, pressure is applied to cells sufficient to disrupt intercellular adhesion). To determine whether kidney epithelial cells released an autocrine growth factor into the medium after wounding, conditioned culture medium was removed from the culture dish after scrape-wounding a monolayer of BSC-1 cells. An aliquot was assayed for any growth-promoting activity on a nonwounded "detector" culture ($1.2 \times 10^6$ cells per 55-m dish).

Growth Promoting Activity of the Factor

Growth-promoting activity in an aliquot of the conditioned medium was assayed by counting the number of cells in a detector culture four days later and comparing the number to that in a control culture to which an aliquot of medium from a nonwounded culture had been added. This strategy showed that wounded kidney epithelial cells of BSC-1 line released a growth-promoting activity that was initially termed "Wound Growth Factor." 3T3 fibroblasts did not produce a similar effect.

For the assay, cells were detached from the dish with a solution of trypsin and an aliquot was counted in a hemocytometer. Confluent cultures were used for this assay so that cells exposed to WGF had a cell count of $2.6 \times 10^6$ cells/culture, whereas cells treated with an aliquot of medium from a non-wounded culture had a count of $2.0 \times 10^6$ cells four days after the additions. Thus WGF stimulated cell proliferation by 30% in this assay. When high-density, quiescent cultures ($3 \times 10^6$ cells/55-mm dish) were used to assay mitogenic activity by measuring [$^3$H]thymidine incorporation into DNA, WGF enhanced DNA synthesis about 60%. To prepare WGF, cells can be scrape-wounded every other day, yet maximal activity will be released into the conditioned medium. WGF is mitogenic for both sparse and confluent cultures of BSC-1 cells, and is stable upon storage at 4° C. to −40° C. for many weeks.

Characterization of Wound Growth Factor Mitogenic Activity

After detection of growth-promoting activity in the conditioned medium of scrape-wounded cultures of BSC-1 cells, efforts to determine size and composition of the mitogenic factor were undertaken. Initially, filters having different molecular weight cut-offs were utilized to show that the growth-promoting activity passed through an Amicon YM membrane having a cut-off of 100 kDa, but was retained by a membrane with a cut-off of 30 kDa, suggesting the size of the mitogenic factor was greater than 30 kDa, but less than 100 kDa. These membranes provide only a very crude estimate of size of the mitogenic factor.

Experiments strongly suggested that the activity was a protein because it could be destroyed by exposure to trypsin (100 μg/ml for 3 hours), dithiothreitol (65 mM for 1 hour), acetic acid (1 M for 5 hours), or by heat (70° C. for 20 minutes).

Characterization of the net electrical charge on WGF was sought using DEAE and CM cellulose matrices (Pharmacia) that have different charges. Results indicated that WGF was cationic. Subsequent experiments indicated that it bound tightly to a heparin cartridge (Pharmacia Hi Trap Heparin) from which it could be eluted with 0.4 to 1.0 M sodium chloride.

Pentosan polysulfate (Sigma Chemical, St. Louis) which is known to block the activity of heparin-binding growth factors such as cidic and basic fibroblast growth factors also blocked activity of WGF suggesting that it is a cationic molecule. Studies on a $C_4$-reversed-phase HPLC column (Vydac) revealed that the protein was markedly hydrophobic in that a concentration of 55% acetonitrile (J. T. Baker, HPLC grade) was required to elute WGF-growth-promoting activity from the column. WGF activity was also stable in 0.1% trifluoroacetic acid (TFA) (J. T. Baker, HPLC grade) and isopropanol.

Certain mitogenically-active fractions of WGF eluted from a $C_4$ reversed-phase HPLC column also bind to concanavalin A-Sepharose 4B (Pharmacia LKB), and are eluted by alpha-methyl mannoside, suggesting the factor contains carbohydrate. Four fractions from the HPLC column that exhibited maximal growth-promoting activity, including the one that elutes at 55% acetonitrile designated as WGF, were each exposed to concanavalin A-Sepharose and subsequently to alpha-methyl mannoside. The eluate was then assayed for its growth-promoting activity. Fractions that eluted from the HPLC column at 55% and at 49% acetonitrile bound to concanavalin A-Sepharose, were eluted by alpha-methyl mannoside and were fully active. In contrast, fractions that eluted at 46% or 57% acetonitrile, or pure epidermal growth factor used as a control mitogen that is not a glycoprotein did not bind to concanavalin A. These results suggest that native WGF is a glycoprotein.

WGF, Heparin, and Other Growth Factors

Although scrape wounding of a different type of cells, endothelial cells, releases acidic fibroblast growth factor (aFGF), characterization of kidney cell WGF indicated that WGF differed from aFGF. Evidence for this is as follows: (1) heparin (Sigma) augments the mitogenic activity of WGF but inhibits aFGF when each component is added to BSC-1 cells, (2) keratan sulfate (a glcosaminoglycan component of the extracellular matrix) stimulates mitogenic activity of WGF but has no effect on activity of aFGF, (3) the mitogenic effects of maximal concentrations of WGF and aFGF are additive, and (4) the size of WGF is about 45 kDa whereas aFGF is about 16 kDa.

WGF also differs from basic FGF (bFGF) in that (1) bFGF (Gibco/BRL) elutes from a heparin affinity column at 1.5 to 1.6 M NaCl whereas WGF elutes at 0.4 to 1.0 M NaCl, and (2) the mitogenic activity of bFGF is 90% inhibited by 55% acetonitrile/0.1% (TFA) which has no effect on the activity of WGF. Furthermore, aFGF and bFGF mRNA are not detected by Northern blotting of BSC-1 cells, indicating that genes encoding these growth factors are not expressed in the cells.

The mitogenic effects of maximal concentrations of partially-purified WGF and epidermal growth factor (EGF, Promega) are also additive, indicating that they probably exert their mitogenic effects by different receptors and signaling pathways.

Treatment of a confluent monolayer of BSC-1 cells with the enzyme heparinase I (Sigma), but not heparinase III (Sigma), releases WGF mitogenic activity from cells into the culture media. However, this seems to deplete WGF, at least temporarily. When cells are first treated with heparinase I, rinsed, the media aspirated, and the monolayer is then scrape-wounded, no growth-promoting activity is detected in the conditioned media. These observations suggest a role for a heparin-like molecule such as a glycosaminoglycan that mediates the association of WGF to the plasma membrane from which it is released upon wounding or treatment with heparinase I.

If WGF resides on the cell surface, it appears to be protected from degradation by trypsin, possibly by carbohydrate residues linked to its protein backbone, and/or by associating with glycosaminoglycans adherent to the plasma membrane (glycocalyx). Evidence in favor of this formulation is derived from the following experiment. A cell monolayer was exposed to the proteolytic enzyme tyrpsin (1 or 10 µg/ml) for 10 minutes. The enzyme was previously shown to have the capacity to destroy WGF activity. Then soybean trypsin inhibitor (10 µg/ml) was added to neutralize the enzyme. When the cell monolayer was subsequently wounded, full biologically active WGF was released into the culture medium indicating that exogenous trypsin had not destroyed growth factor associated with the cells.

WGF does not appear to be stored by the cells in extracellular matrix (ECM). This conclusion is based on the following experiment. A confluent monolayer of BSC-1 cells is detached from ECM by addition of EGTA (J. T. Baker) to the medium, leaving a coating of ECM on the surface of the culture dish. Fresh medium was added to the dish and its ECM coating was then subjected to scrape-wounding. No mitogenic activity was detected in the conditioned medium, suggesting that the activity resided on or within the cells and not in the ECM.

The mitogenic potency of partially-purified WGF is equivalent to the mitogenic potency of about 5% calf serum, or 20 pg/ml a FGF, or 20 pg/ml basic FGF, or 15 ng/ml EGF, using assays disclosed herein.

Comparison of Known Growth Factors to WGF-Derived Peptide; Additive Effects.

The mitogenic potency of the 14-amino acid peptide AQPYPQGNHEASYG (SEQ ID NO: 15) having a serine residue at position 12 (14-Ser) was compared to growth factors and other mitogenic signals for monkey kidney epithelial cells of the BSC-1 line. The previously identified maximal mitogenic concentration of each growth-promoting signal was employed, and compared to the WGF-derived peptide at concentrations from 0 to 0.5 µg/ml.

The following peptide and ionic mitogenic signals were studied: epidermal growth factor (EGF), 50 ng/ml; insulin-like growth factor-I (IFG-I), 50 ng/ml; acidic fibroblast growth factor (FGF-1), 100 pg/ml; basic fibroblast growth factor (FGF-2), 1,000 pg.ml; vasopressin, 75 pg/ml; calf serum (0–1%); high potassium medium (5 mM added KCl, final concentration 10.4 mM), high sodium medium (25 mM of NaCl added, final concentration 180 mM).

Nontransformed monkey kidney epithelial cells of the BSC-1 line were grown to confluence in Dulbecco's modified Eagle's medium containing 1% calf serum and 1.6 µm biotin in 55-mm culture dishes at 38° C. in a $CO_2$ incubator. When cells achieved a density of about $10^6$ per dish, the spent medium was removed and replaced with fresh medium containing 0.5% calf serum and the 14-amino acid peptide (0.5 µg/ml). Additions of each of the mitogenic signals at maximal concentration were made to the culture medium. Four days later the number of cells in each culture was counted in a hemocytometer. Values obtained were the mean of 3 separate cultures. Doubling the calf serum concentration from 0.5% to 1.0% did not significantly alter the growth of BSC-1 cells. Addition of the 14-Ser peptide (0.5 μg/ml) stimulated growth by 25–30% at each of these serum concentrations.

1. Comparisons with EGF, IFG-1, Acidic FGF, Basic FGF, Vasopressin

The "14-Ser Peptide" AQPYPQGNHEASYG (SEQ ID NO: 15) increased cell number by 25–30% compared to control at four days. EGF (50 ng/ml) alone stimulated growth by 31% in the absence of "the 14-Ser peptide," and by 61% in its presence, indicating that the two mitogens were additive.

IFG-I (50 ng/ml) stimulated growth by 20%; it was less potent than the 14-Ser peptide. When both were added a 38% stimulation was observed. Although less than the expected 45% if fully additive, the mitogenic effect of IGF-I appeared additive to that of the 14-Ser peptide.

Acidic FGF (100 pg/ml), basic FGF (1,000 pg/ml), and vasopressin (75 pg/ml) stimulated growth by 17%, 18%, and 14%, respectively, compared to the 14-Ser peptide which increased cell number by 25%. Each of these known peptide growth factors was additive with the 14-Ser peptide peptide; acidic FGF by 44%; basic FGF, 41%; and vasopressin, 36%.

In summary, the 14-Ser peptide WGF-derived peptide is a potent mitogen because it is equivalent to, or more potent than, each of five known peptide growth factors for kidney epithelial cells. In addition, the growth-promoting effect of the 14-Ser peptide was additive with each of the five growth factors suggesting that it acts by a different receptor and/or signal transduction pathway than they do. Finally, the additive mitogenic effects suggest that the 14-Ser peptide, in combination with one or more of the known growth factors, could act in vivo to speed repair and regeneration of the injured kidney during acute renal failure.

2. High Potassium Medium, High Sodium Medium

Raising the potassium concentration from the control value of 5.4 mM to 10.4 mM, or the sodium concentration from 155 mM (control) to 180 mM by addition of the appropriate salt solution serves as a mitogenic signal for kidney epithelial cells.

When the potassium concentration of the culture medium was raised from 5.4 to 10.4 mM by adding a solution of potassium chloride, the cell number was increased by 18%. Addition of the 14-Ser peptide was expected to enhance growth by 43%; an increase of 35% was observed.

Raising the sodium concentration of the medium from 155 mM to 180 mM by addition of sodium chloride solution increased growth by 25%. When the 14-Ser peptide was added an increment in growth of 41% was observed, less than the predicted 50%.

In summary, each of the two ionic mitogenic signals were additive with the 14-Ser peptide mitogen.

3. Time Required for the Growth Enhancing Effect of 14-Ser

To gain additional insight into the affinity of the 14-Ser WGF-derived peptide for the cell surface, experiments were performed to determine the minimum amount of time required for the ligand to be in contact with renal cells to irreversibly commit them to accelerated growth.

Confluent monolayers of BSC-1 cells are prepared as herein and exposed to the 14-Ser peptide (0.5 μg/ml) for different amounts of time (0 to 30 minutes). At the end of the defined exposure period, culture medium containing the mitogen was aspirated, the monolayer was rinsed to remove non-adherent peptide, and fresh medium was added. Four days later the number of cells in the culture was counted.

Exposure of cells to the 14-Ser peptide for 2 minutes was sufficient to commit them to maximal growth stimulation (29%); half-maximal stimulation was at 1 minute. The 40-amino acid peptide (see Table 2) behaved similarly. In contrast, the commitment time for EGF is 4 minutes, and for vasopressin it is 2 minutes. Thus the 14-Ser peptide apparently requires a remarkably short time (2 minutes) to irreversibly bind to the surface receptor and commit cells to accelerated growth. The time required is equivalent to or less than other known peptide mitogens (EGF, 4 minutes; vasopressin, 2 minutes; low sodium growth factor, 5 minutes; high potassium medium, 6 minutes; adenosine monophosphate, 14 hours).

Purification of WGF

A protocol to prepare one Liter of WGF conditioned medium is described herein. The usual yield of WGF protein is about 50 ng per liter as estimated by SDS-polyacrylamide electrophoresis and amino acid compositional analysis.

Conditioned Media Preparation: 100 cultures of BSC-1 cells are grown to confluence ($6$–$8 \times 10^6$ cells) on plastic tissue culture dishes (Nunc) having a diameter of 10 cm in Dulbecco's modified Eagle's medium containing 2% calf serum. The medium is aspirated, and the culture is rinsed with phosphate-buffered saline (PBS) (Sigma) solution to remove medium and serum. Then 10 ml of PBS is added to each dish in preparation for wounding. A total of 5 wounds to the cell monolayer are rapidly made by scraping a 200 μL plastic pipet tip across the surface of the dish from edge to edge. About ten minutes later (9.5 minutes is preferred) the conditioned buffer is decanted into a plastic Nalgene beaker.

Isolation and Purification of WGF: After conditioning, pooled conditioned buffer is sterile-filtered (CoStar, 0.2 μm pore size) to remove any debris or detached cells into silanized (Aquasil, Pierce) glass bottles (Wheaton). The sterile conditioned buffer is diafiltered, desalted, and concentrated using a YM-30 disc membrane (Amicon) at 4° C. The concentrated material is then sterile filtered (Millex HA, 0.45 Fm) at room temperature, loaded onto a 1 ml heparin-affinity cartridge and eluted with a solution of 1 M NaCl. The cartridge is first exposed to 0.4 M NaCl in 10 mM sodium phosphate (pH 7.4) to elute nonmitogenic material; the same buffer containing 1 M NaCl is then used to elute mitogenic activity from the cartridge. The eluate is desalted, and the volume is reduced using a Centricon 3 filter (Amicon) by centrifugation (7500 g for 2 hours at 4° C.). The concentrate (300–400 μl) is loaded onto a $C_4$-reversed phase HPLC column (250 mm×4.6 mm, particle size 5 μm) (Vydac), and is eluted with a gradient of acetonitrile (1–80%) in trifluroacetic acid (0.1%) (TFA) for 50 minutes using a Beckman Gold Chromatographic System. At least 5 different protein peaks (monitored by absorbance at 214 nm) that exhibit mitogenic activity can be readily identified. However, the peak that elutes at ~55% acetonitrile routinely exhibits the most mitogenic activity and reproducibility in different isolates. This eluate is collected by hand into a silanized Eppendorf tube, loaded onto a $C_8$ column (Vydac), and rechromatographed using the same acetonitrile/TFA gradient described above. Again the mitogenic activity elutes at ~55% acetonitrile. Growth-promoting activity and total protein content is monitored at each step during the purification process. Depending upon the number of liters of conditioned buffer processed, it may be necessary to run a second $C_8$ column to optimize separation of the peak of interest. This bioactive material is then reduced in volume using a vacuum concentrator (Savant), and subsequently loaded onto a 12.5% SDS gel for electrophoretic separation.

The $M_r$ of WGF is estimated by comparison of its electrophoretic migration to that of standard proteins of known molecular size. Different proteins in the gel are visualized by staining with silver (BioRad), or after blotting onto a PVDF membrane (Millipore) and staining the blot with Coomassie blue dye (Gibco/BRL). More than one band usually appears. To determine which band represented the mitogenic form of WGF, an unstained nonreducing gel was sliced into 2-mm wide fragments after electrophoresis, and each was eluted for 18 hours with agitation at room temperature in PBS containing acetonitrile (3%) and bovine serum albumin (0.1%). The eluate of each fragment was added to a culture of BSC-1 cells to determine its capacity to stimulate cell growth. This experimental strategy revealed that the active WGF proteins had a $M_r$ of 22 and 45 kDa.

WGF appears to be released from cells after wounding; it does not appear in the culture medium of nonwounded cultures. Evidence in support of this conclusion was obtained by the following experiment. Conditioned buffer (1550 ml) from scrape-wounded cultures was obtained as described above and resulted in a $C_8$-HPLC peak that eluted at 55% acetonitrile and exhibited growth-promoting activity, whereas the same volume (1550 ml) of buffer exposed to nonwounded cultures subjected to the same purification protocol did not display this protein peak or mitogenic activity.

$NH_2$-Terminal Sequence of Wound Growth Factor

To obtain the amino acid sequence of the $NH_2$-terminus of WGF, 2.5 μg of $C_8$-purified protein was obtained and subjected to electrophoresis on a 12.5% SDS-polyacrylamide gel. The relative electrophoretic mobility of the purified protein was compared to that of standard proteins of known molecular size. After blotting onto a PVDF membrane (millipore) and staining with Cooomassie Blue dye, two bands were seen corresponding to sizes of 45 kDa and 22 kDa. They were subsequently cut out of the blot and then loaded onto an ABI microsequencer. The results of microsequencing are expressed using conventional abbreviations and symbols for the amino acid listed below:

| Amino acid | Three-letter abbreviation | symbol |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| x | identity not determined | x |
| pyroglutamic acid | | pE |
| methionine amide | | M-$NH_2$ |

A total of four determinations of the amino-terminal sequence of WGF have been made on different batches of conditioned media. The first fourteen amino acids of the 45 kDa protein in the amino- to carboxy-orientation ($NH_2 \rightarrow COOH$) are, wherein the numbers refer to positions using the first amino acid as number one:

```
              1             5            10  12    14
          NH2-A  Q  P  Y  P  Q  G  N  H  E  X  A/S  Y  G-COOH        (SEQ ID NO: 1)

Determination of the sequence of three different isolates
of the 22 kDa protein are:

1             5            10              16
          NH2-A  Q  P  Y  P  Q  G  N  H  E  A  T  S  S  S  F-COOH    (SEQ ID NO: 4)

NH2-A  Q  P  Y  P  Q  G  N  H  E  A  T  S  S/Y-COOH        (SEQ ID NO: 32)

NH2-A  Q  P  Y  P  Q  G  N  H  E  A  T-COOH                (SEQ ID NO: 7)
```

The longest is 16 amino acids.

Importantly, the first 10 amino acids are identical in each of the four sequence determinations, suggesting that the 22 kDa protein could be a fragment or breakdown product of the 45 kDa protein. However, the different sequences of amino acids 12 to 14 in the 22 and 45 kDa proteins suggest that they could represent two WGF isoforms.

The NH$_2$-Terminal Domain of WGF is Mitogenic for Kidney Epithelial Cells

A sequence of the eleven NH$_2$-terminal amino acids AQPYPQGNHEA (11-mer) (SEQ ID NO: 6) of the 22 kDa protein was used to prepare a synthetic peptide linked to a branched lysine core. This multiple antigenic peptide system (MAPS) was used to immunize animals to prepare a polyclonal antibody that would recognize WGF. The MAPS protein has a polylysine backbone that is attached to a resin at one end and has four branches at the other; each branch is ligated to one molecule of the 11-mer peptide. Surprisingly, when tested for growth-promoting activity, the MAPS peptide stimulated DNA synthesis and proliferation of monkey kidney epithelial cells of the BSC-1 line. Its maximal growth-promoting effect was similar to that of native WGF. When compared to a MAPS protein prepared from a different 11 amino acid sequence and another one prepared using an unrelated 16 amino acid sequence, only the sequence based on WGF protein exhibited mitogenic activity. In subsequent experiments, it was shown that the 11-amino acid peptide, in the absence of the branched lysine core, stimulated proliferation of these kidney cells to the same extent as did purified WGF protein. Based on two cell types tested, the 11-mer WGF peptide stimulated mitogenic activity of renal epithelial cells but did not stimulate growth of murine 3T3 fibroblasts.

In addition, the growth-promoting effect of the 11-mer peptide and of wound conditioned buffer were not additive, suggesting that the 11-mer peptide stimulates cell proliferation by the same receptor and signaling pathway as does intact WGF. These unexpected results suggest that the 11 amino acids of the NH$_2$-terminus represent a mitogenic domain of WGF, although other growth-promoting domains may be contained in the native protein whose estimate length is about 400 amino acids.

FIG. 1 shows equivalent mitogenic dose responses of a synthetic 11-mer peptide, AQPYPQGNHEA (SEQ ID NO: 6) which represents native (22 kDa) amino-terminal WGF, and the most active hexapeptide synthesized of the present invention YPEGNH (SEQ ID NO: 33), which differs from native WGF by replacement of a glutamine (Q) (charge=0) residue with glutamic acid (E) (charge=−1). However, the native sequence is preferred (see Table 2). The "native" sequence is that found in the 22 or 45 kDa WGF as obtained from cultured cells. The peptides are purified by reversed-phase HPLC on a C$_{18}$ column using a gradient of acetonitrile (1–80%) in 0.1% trifluroacetic acid, lyophilized, and then dissolved in tissue culture medium.

Nontransformed monkey kidney epithelial cells of the BSC-1 line were grown to confluence in Dulbecco's modified Eagle's medium containing 1% calf serum and 1.6 μM biotin at 38° C. in a CO$_2$ incubator. When cells achieved a density of about 10$^6$ per dish, the spent medium was removed and replaced with fresh medium containing 0.5% calf serum and different amounts of the two peptides. Four days later the number of cells in each culture was counted. Each value is the mean of 3 separate cultures.

Mitogenicity of WGF-Derived Peptides

To delineate the sequence of the smallest peptide that could stimulate renal cell growth, synthetic peptides of different lengths were prepared (see below), and purified by reversed-phase HPLC on a C$_{18}$ column. Mitogenic activity was assessed in a culture of BSC-1 cells by counting the number of cells after exposure to a specified concentration (0.5 to 20 μg/ml) of peptide for four days, and comparing the result to growth in the absence of added peptide.

Peptides

```
                   1   5    10
WGF 11-mer:  NH2-AQPYPQGNHEA-COOH   (SEQ ID NO: 6)

9-mer:            QPYPQGNHE          (SEQ ID NO: 20)

8-mer:            PYPQGNHE           (SEQ ID NO: 23)

7-mer:            PYPQGNH            (SEQ ID NO: 25)

7-mer:             YPQGNHE           (SEQ ID NO: 26)

6-mer:             YPQGNH            (SEQ ID NO: 2)
```

Like the 11-mer, each of five shorter peptides, (6 to 9 amino acids long) stimulated renal cell growth maximally to the same extent (25–30%) as did native WGF.

The following peptides (4 to 6 amino acids long) represent domains of NH$_2$-terminal WGF that did not stimulate cell growth, as compared to the active 11-mer of line 1:

```
                   1   5    10
WGF11-mer:   NH2-AQPYPQGNHEA-COOH   (SEQ ID NO: 6)

6-mer:            QPYPQG             (SEQ ID NO: 34)

4-mer:                GNHE           (SEQ ID NO: 34)

5-mer:              PQGNH            (SEQ ID NO: 36)

5-mer:             YPQGN             (SEQ ID NO: 3)
```

The following 6-mer and 7-mer peptides whose sequences/differ from WGF also did not stimulate cell growth:

```
6-mer:     YPRGNH      (SEQ ID NO: 37)

7-mer:     LKYSGQD     (SEQ ID NO: 38)
```

The results presented above indicate that maximal mitogenic activity of peptides based on the native sequence resides in a 6-mer whose sequence is YPQGNH (SEQ ID NO: 2) because:

(1) peptides containing this sequence that are 7, 8, 9 or 11 amino acids long stimulate growth to the same extent, (2) each of the two 5-mers that lack one amino acid from either the NH$_2$— or —COOH terminus of the 6-mer are not mitogenic to the same extent, (3) a 6-mer (YPRGNH) (SEQ ID NO: 37) that differs from YPQGNH (SEQ ID NO: 2) in only a single amino acid is not mitogenic to the same extent, (4) another 6-mer (QPYPQG) (SEQ ID NO: 34) that differs from YPQGNH (SEQ ID NO: 2) in two amino acids is not mitogenic, and (5) neither a 4-mer (GNHE) (SEQ ID NO: 35) whose sequence is found in WGF, nor a 7-mer (LKYSGQD) (SEQ ID NO: 38) having an unrelated sequence, is mitogenic.

Thus the NH$_2$-terminus of native WGF contains an hexapeptide sequence, NH$_2$-tyrosine-proline-glutamine-glycine-asparagine-histidine-COOH (SEQ ID NO: 2), that is mitogenic for renal epithelial cells, as exemplified by the BSC-1 line.

Peptides of various lengths are also within the scope of the present invention, as long as the mitogenic hexamer sequence is included. Peptides of various lengths may be used individually or combined in various ways for specific purposes. These possibilities include (NH$_2$-terminus→COOH terminus):

```
AQPYPQGNHEATSSSF    (SEQ ID NO: 4)
AQPYPQGNHEATSSS     (SEQ ID NO: 5)
AQPYPQGNHEATSS      (SEQ ID NO: 9)
AQPYPQGNHEATS       (SEQ ID NO: 8)
AQPYPQGNHEAT        (SEQ ID NO: 7)
   YPQGNHEATSSSF    (SEQ ID NO: 27)
   YPQGNHEATSSS     (SEQ ID NO: 28)
   YPQGNHEATSS      (SEQ ID NO: 29)
   YPQGNHEATS       (SEQ ID NO: 30)
   YPQGNHEAT        (SEQ ID NO: 31)
AQPYPQGNHEA         (SEQ ID NO: 6)
AQPYPQGNHE          (SEQ ID NO: 14)
 QPYPQGNHEA         (SEQ ID NO: 18)
AQPYPQGNH           (SEQ ID NO: 19)
 QPYPQGNHE          (SEQ ID NO: 20)
 PYPQGNHEA          (SEQ ID NO: 21)
 QPYPQGNH           (SEQ ID NO: 22)
 PYPQGNHE           (SEQ ID NO: 23)
  YPQGNHEA          (SEQ ID NO: 24)
   PYPQGNH          (SEQ ID NO: 25)
   YPQGNHE          (SEQ ID NO: 26)
```

These peptides may be combined with other amino acid sequences at either end or both ends (NH$_2$ and COOH).

Characterization of Native and Modified WGF-Derived Amino-Terminal Peptides

Amino acid replacements in the amino-terminus of native WGF were identified that could alter peptide mitogenic activity. The objective of this effort was to maximize the growth-promoting activity of the peptide for use in studies of its efficacy in treatment of acute renal failure in animal models of the syndrome. The strategy was to design and then chemically synthesize diverse peptides by substituting structurally related amino acids for those found in the native WGF sequence. The peptide of interest was then purified on a reversed-phase $C_{18}$ column HPLC as described herein using a gradient of 1–80% acetonitrile in 0:1% trifluroacetic acid (TFA). The purified peptide was then lyophilized to remove the acetonitrile and TFA and the lyophilized powder was weighed, dissolved in buffer and added to the culture medium to measure its effect on the growth of monkey kidney epithelial cells as described herein. To compare the relative potency of different peptides, only those molecules that stimulated growth maximally after 4 days in culture by 25–30% were analyzed further by defining their concentration-dependence. A value termed the $K_{1/2}$, was used. This term is defined herein as the peptide concentration in micromoles (μM) at which the growth-stimulating effect is one-half the concentration at which maximal proliferation is observed. The lower the value the greater the mitogenic potency of the peptide.

TABLE 2

Relative Potency of WGF-Derived Peptides on Growth of Kidney Epithelial Cells

| | Peptide Amino Acid Sequence | | Growth-Stimulation $K_{1/2}$, μM |
|---|---|---|---|
| 14-mer: | AQPYPQGNHEASYG | (SEQ ID NO: 15) | 0.126 |
| | AQPYPQGNHEASYG + keratan sulfate | | 0.067 |
| | AQPYPQGNHEASYG + heparin | | 0.040 |
| | AQPYPEGNHEASYG | (SEQ ID NO: 39) | 0.128 |
| | AQPYPQGNHEAAYG | (SEQ ID NO: 11) | 0.199 |
| | AQPYPQGNHEAAYG + keratan sulfate | | 0.054 |
| 11-mer: | YPQGNHEASYG | (SEQ ID NO: 40) | 0.166 |
| | YPQGNHEASYG + heparin | | 0.166 |
| | AQPYPQGNHEA | (SEQ ID NO: 6) | 0.260 |
| | AQPYPEGNHEA | (SEQ ID NO: 41) | 0.206 |
| 6-mers: | YPQGNH | (SEQ ID NO: 2) | 0.352 |
| | YPEGNH | (SEQ ID NO: 33) | 0.301 |
| | YPEGDH | (SEQ ID NO: 42) | 11.03 |
| | YPEGKH | (SEQ ID NO: 43) | 14.10 |
| | FPEGNH | (SEQ ID NO: 44) | 2.72 |

TABLE 2-continued

Relative Potency of WGF-Derived Peptides on Growth of Kidney Epithelial Cells

| Peptide Amino Acid Sequence | | Growth-Stimulation $K_{1/2}$, μM |
|---|---|---|
| | YPQGNH-amide | 8.85 |
| 16-mer: | AQPYPQGNHEATSSSF (SEQ ID NO: 4) | 0.218 |
| 40-mer: | AQPYPQGNHEAQPYPQGNHEAQPYPQGNHEAQPYPQGNHE (SEQ ID NO: 49) | 0.007 |

Amino acids designated by capitals are those present in native WGF, whereas the bold letters refer to conservative amino acid substitutions.

The results summarized in Table 2 indicate that it is longer peptides (40-mer>14-Mer>11-mer>6-mer) containing the sequence YPQGNH (SEQ ID NO: 2), that are the most potent. The longest non-repeating most potent peptide tested is the 14-mer AQPYPQGNHEASYG (SEQ ID NO: 15), i.e., it has the lowest $K_{1/2}$, 0.126 μM. Note that exposure of the cells for 5 minutes to the glycosaminoglycan, keratan sulfate (2 μg/ml) prior to addition of the peptide, enhances the potency ($K_{1/2}$=0.067 μM) and heparin (1 μg/ml) is even more effective (0.040 μM). In rat studies the 14-mer was also effective in increasing survival of rats in which ARF was induced by mercuric chloride. The 14-mer with serine in position 12 was more effective than the 11-mer with glutamic acid in position 6.

The length of the 14-mer AQPYPQGNHEASYG (SEQ ID NO: 15) provoked interest about the three-dimensional structure of the peptide. Circular dichroism was carried out and revealed a spectrum consistent with a beta-pleated sheet conformation.

It is of interest that the potency of the 11-mer peptide AQPYPQGNHEA (SEQ ID NO: 6) (native WGF sequence) is similar to that of the synthetic hexapeptide YPEGNH (SEQ ID NO: 33) ($K_{1/2}$~0.3 μM) which has a single substitution: glutamic acid (E) replacing the native glutamine (Q). Several highly conservative modifications of the 6-mer sequence result in drastic reductions in potency: replacement of the tyrosine (Y) residue with phenylalanine (F), substitution of asparagine (N) with aspartic acid (D) or lysine (K), or amidation of the carboxy-terminus.

Evidence to support the hypothesis that WGF and its peptides exert their mitogenic effect via a cell surface receptor mechanism was obtained by showing that pentameric peptides that lack one amino acid at either terminus of the hexapeptide YPQGNH (SEQ ID NO: 2), block the proliferative effect of intact hexamer. In these studies the pentamers, PQGNH (SEQ ID NO: 36) or YPQGN (SEQ ID NO: 3) were synthesized, purified by HPLC and then assayed for growth-promoting activity. Neither was mitogenic. When either pentamer was added to the cell culture medium, it blocked the capacity of the hexamer YPQGNH (SEQ ID NO: 2) added at the same time or afterwards to stimulate cell growth. These observations suggest that the pentamers and the hexapeptide compete for the same binding site/receptor on the plasma membrane. Because the pentamers are not mitogenic, when they bind to the site, growth is not observed. After pentamers are bound to the site, the pentamers appear to prevent the hexapeptide from gaining access to the membrane.

Additional evidence that the peptides have a high potency for renal epithelial cells was obtained by defining the time required for interaction between peptide and cells for irreversible commitment to accelerated proliferation. In these experiments a solution containing the peptide of interest was added to the cell monolayer; culture medium was then aspirated at a specified time thereafter. Then fresh medium without the peptide was added and the number of cells was counted four days later. Contact of the cells with the peptide YPQGNH (SEQ ID NO: 2) for 2 minutes resulted in maximal growth-promoting activity, whereas the peptide could be completely washed off the cells at earlier times (0.5, 1, or 1.5 minutes) without stimulating growth. When the cells were exposed to keratan sulfacte (2 μg/ml) for 5 minutes before adding the peptide, only 1 minute of exposure was necessary for the maximal mitogenic effect to be observed. Similar results were obtained when the peptide YPEGNH (SEQ ID NO: 33) was tested; 3 minutes of exposure was sufficient to obtain a maximal growth response, but only 1.5 minutes when the cells were pre-treated with keratan sulfate. Thus, keratan sulfate enhances the mitogenic potency of not only native WGF protein by WGF-derived peptides as well.

A search of the seven protein sequence databases (Blaster) operated by NCBI reveled that the $NH_2$-terminal sequence of WGF is novel and has limited homology with two known mitogenic proteins, gastrin releasing peptide (GRP) and bombesin, as shown below, using as the first position the first amino acid of the $NH_2$ terminus:

```
                              1        10        20      27
           human GRP:    VPLPAGGGTVLTKMYPRGNHWAVGHLM-NH2   (SEQ ID NO: 45)

porcine GRP:  APVSVGGGTVLAKMYPRGNHWAVGHLM-NH2   (SEQ ID NO: 46)

1    5      10    16
           WGF:     45 kDa           AQPYPQGNHEXAYG        (SEQ ID NO: 1)
```

```
                     5
22 kDa        AQPYPQGNHEATSSSF       (SEQ ID NO: 4)

bombesin:     pEQRLGNQWAVGHLM-NH2    (SEQ ID NO: 47)
              1         10  14
```

Symbols for amino acids in bold type represent identities between different proteins.

Alignment between the 14 amino acids of the NH$_2$-terminus of WGF and the bombesin molecule is limited to the consecutive GN residues (amino acids #7, 8 in the 14 amino acid active peptide of WGF; #5, 6 in bombesin), and an A residue (amino acid #11 in WGF; #9 in bombesin). Previous reports (Broccardo, et al., 1975; and Heimbrook et al., 1998) indicate that the seven COOH-terminal amino acids of bombesin and of GRP are identical (WAVGHLM-amide) (SEQ ID NO: 48), and are also the locus of mitogenic activity in these two proteins. A synthetic peptide comprising this sequence of amino acids is mitogenic for BSC-1 cells, but its $K_{1/2}$ is ~10 µM. Importantly, the mitogenic sequence of these seven COOH-terminal amino acids is not found in the mitogenic 16 amino acids of the NH$_2$-terminus of WGF.

The functional differences between WGF and other known sequences include that the hexapeptide YPQGNH (SEQ ID NO: 2) is mitogenic for renal epithelial cells, whereas the GRP-derived hexapeptide YPRGNH (SEQ ID NO: 37) is at most borderline mitogenic (10% stimulation) for renal epithelial cells and is not reported to be necessary for mitogenic stimulation of fibroblasts.

It is of interest that the mitogenic hexapeptide derived from the NH$_2$-terminus of WGF, YPQGNH (SEQ ID NO: 2) (amino acids #4 to 9), differs in only a single amino acid (Q→R) from an hexapeptide sequence in human and porcine GRP, YPRGNH (SEQ ID NO: 37) (amino acids #15 to 20), a domain that is not known to be mitogenic (Heimbrook et al., 1988). There is no prior teaching or suggestion to make an amino acid substitution at this position, no suggestion to make the particular substitution that is in WGF, nor any such a suggestion that substitution would confer mitogenic-stimulating activity on WGF.

These results indicate that the WGF-derived hexapeptide, YPQGNH (SEQ ID NO: 2), is a novel mitogen for renal epithelial cells.

Further Characterization of Mitogenic Peptides Derived from the NH$_2$-Terminus of Wound Growth Factor As discussed in previous section, purification of the Wound Growth Factor (WGF) from conditioned medium of scrape-wounded monkey kidney epithelial cells (BSC-1 line) revealed two mitogenic proteins; 22 kDa and 45 kDa on sodium dodecylsulfate-polyacrylamide gel electrophoresis (SDS-PAGE). Microsequencing of the NH$_2$-termini of these proteins suggested that they may be isoforms because the first 10 amino acids of each were identical. A total of 16 amino acids were identified at the NH$_2$-terminus of the 22 kDa isoform, and 14 for the 45 kDa isoform. However, for the 45 kDa isoform, the amino acid at position 11 was not identified, and at position 12, alanine or serine were equivalent designations.

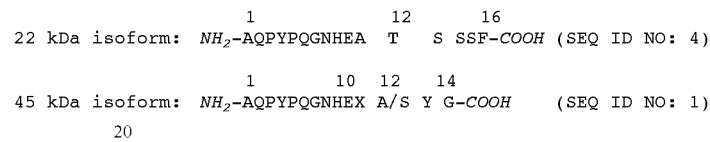

Peptides of various lengths are within the scope of the present invention, as long as the mitogenic hexamer sequence, NH$_2$-tyrosine-proline-glutamine-glycine-asparagine-histidine-COOH (YPQGNH) (SEQ ID NO: 2) is included.

Amino acid replacements were identified in the amino-terminus of native WGF that could maximize the growth-promoting activity of the peptide for use in studies of its efficacy in treatment of acute renal failure in a rat model of this syndrome. The strategy was to design and then chemically synthesize diverse peptides by substituting structurally related amino acids for those found in the native WGF sequence.

The peptide of interest was then purified on a reversed-phase $C_{18}$ HPLC column using a gradient of 1–80% acetonitrile in 0.1% trifluroacetic acid (TFA). The purified peptide was then lyophilized to remove the acetonitrile and TFA and the lyophilized powder was weighed, dissolved in buffer and added to the tissue culture medium to measure its effect on growth of monkey kidney epithelial cells.

To compare the relative potency of different peptides, only those molecules that stimulated growth maximally after 4 days in culture by 25–30% were analyzed further by defining their concentration-dependence. A value termed the $K_{1/2}$, was used. This term is defined herein as the peptide concentration in micromoles (µM) at which the growth-stimulating effect is one-half the concentration at which maximal proliferation is observed. The lower the value, the greater the mitogenic potency of the peptide.

Table 2 indicates that the 14-amino acid peptide AQPYPQGNHEASYG (SEQ ID NO: 15) with a serine residue at position 12 (14-ser) ($K_{1/2}$=0.126 µM) is a more potent mitogen than AQPYPQGNHEAAYG (SEQ ID NO: 11) having an alanine residue in that position ($K_{1/2}$=0.199 µM). When the glycosaminoglycan keratan sulfate was added at a concentration of 10 µg/ml the mitogenic potency was enhanced because the $K_{1/2}$ fell to 0.067 µM. In addition, the glycosaminoglycan heparin, added at a concentration of 1 µg/ml was even more effective, reducing the $K_{1/2}$ to 0.040 µM. At the optimal concentrations employed in these experiments, a molecular ration of 1 peptide molecule: 1 glycosaminoglycan (GAG) molecule was added to the cells for either keratan sulfate or heparin. The stimulatory effect of glycosaminoglycans was mediated by formation of a peptide-GAG complex via ionic bonds (cationic histidine of peptide to anionic sulfate of either GAG) or by hydrogen bonding (hydroxyl groups of serine/tyrosine of peptide to oxygen residue of GAG carbohydrate). The peptide-GAG complex could stabilize/facilitate binding of the peptide to its receptor on the cell surface, as has been proposed to explain the enhanced mitogenic effect of acidic fibroblast growth factor (FGF-1) with heparin that has been observed with diverse types of cells. Replacement of a glutamine (Q) residue in position 6 with a glutamic acid residue (E) did not alter mitogenic potency of 14-Ser peptide ($K_{1/2}$=0.128 µM), although this replacement strategy does reduce the $K_{1/2}$ for the 6-amino acid peptide YPQGNH (SEQ ID NO: 2) ($K_{1/2}$=0.352 to 0.301 µM), and for the 11-amino acid peptide AQPYPQGNHEA (SEQ ID NO: 6) ($K_{1/2}$=0.260 to 0.206 µM).

Shorter peptides of all 11 amino acid in length such as AQPYPQGNHEA (SEQ ID NO: 6) ($K_{1/2}$=0.260 µM), and 6 amino acids, YPQGNH (SEQ ID NO: 2) ($K_{1/2}$=0.332 µM) each lack the SYG terminal amino acids of the 14-amino acid peptide AQPYPQGNHEASYG (SEQ ID NO: 15) ($K_{1/2}$=0.126 µM), and are less potent as mitogens. To determine if an 11 amino acid peptide containing the SYG sequence was required for maximal mitogenesis, a peptide with the sequence YPQGNHEASYG (SEQ ID NO: 40) was synthesized, purified, and then assayed for activity. Interestingly its $K_{1/2}$ was 0.166 µM in the absence or presence of heparin, indicating that the fall 14 amino acid length was required for the maximal mitogenic effect.

A peptide synthesized using the longest known WGF sequence, that 16 amino acids of the 22 kDa isoform, AQPYPQGNHEATSSSF (SEQ ID NO: 4), was also tested for its mitogenic activity ($K_{1/2}$=0.218 µM). It was not as potent as the 14-amino acid peptide AQPYPQGNHEASYG (SEQ ID NO: 15) derived from the NH$_2$-terminus of the 45 kDa isoform.

Finally, a 40-amino acid peptide was synthesized. It is a tetramer of the first 10 amino acids which are identical in the 22 kDa and the 45 kDa isoforms of WGF. This is the most potent WGF peptide yet identified, having a $K_{1/2}$=0.007 µM. The enhanced mitogenic potency is presumably related to its relatively great length which could stabilize ligand binding at the cell surface receptor site by ionic or hydrophobic interactions, and/or hydrogen bonding. Ultimately, it may prove the most efficacious WGF-derived peptide under clinical conditions because of its great potency.

The 14-amino acid peptide (14-Ser), because of its high mitogenic potency and relatively short length, was chosen for further studies in cells, and for use in the treatment of rats with mercuric chloride-induced acute renal failure.

An Antibody to the Factor

The 11 amino acids of the NH$_2$-terminus of WGF were used to prepare two different conjugated peptide antigens. One was the MAPS protein described above in which the 11-mer peptide was linked to a branched polylysine backbone, and the other was a conjugate in which the 11-mer was chemically joined to keyhole limpet hemocyanin (KLH). The MAPS protein and KLH-conjugate were used to immunize rabbits. The antibody that results from these strategies serves to detect native WGF protein in urine, serum, and tissue, and could also be used to obtain a cDNA clone encoding WGF by immunoscreening a kidney epithelial cell cDNA library in λgt11.

Lack of immuogenicity of the peptide would favor its clinical utility in the treatment of renal diseases such as acute renal failure.

Product Relevance of the WGF-Derived Mitogenic Hexapeptide

The synthetic hexapeptide, like native WGF, can be used to treat acute renal failure, chronic renal diseases, and renal cell cancer. Because preparation of an antibody to an hexapeptide may not be readily successful because of its small size, a goat or rabbit antibody against the 11-mer or a larger peptide may be preferred to detect WGF in urine, serum, and tissue of patients with renal diseases.

Production of WGF by Recombinant Genetic Methods

An appropriate vector to express WGF from the nucleotide sequence encoding a full-length clone depends in part upon whether glycosylation of the protein is required for each of its biological effects. If WGF is not glycosylated, a bacterial expression system may prove suitable, but if carbohydrate is definitively detected and shown to be required for full activity, then a mammalian expression system such as Chinese Hamster Ovary (CHO) cells would be appropriate.

Because the synthetic 14-mer peptide, indeed an hexamer of the amino-terminus is mitogenic, it appears that glycosylation of the protein is not required for mitogenic activity. However, glycosylation could prove to be an important determinant in modulating the turnover (half-life) of the protein in vivo. This is the case for erythropoietin, for example.

A nucleotide sequence encoding for at least the mitogenic hexamet is prepared, linked to suitable regulatory elements, and incorporated into an expression vector. A host cell is transformed with the vector, and the host is placed in conditions suitable for expression. After expression of the WGF gene or partial nucleotide sequence in a recombinant host, the recombinant protein is isolated from the culture medium by using an antibody-affinity column prepared by conjugating an antibody to WGF to an appropriate matrix. This preparative strategy should yield large quantities of the recombinant protein.

Alternatively, and more simply, sufficient amounts of the NH$_2$-terminal 14-ser, 11 amino acid peptide, the hexapeptide YPQGNH (SEQ ID NO: 2), or other peptides expressing full mitogenic potency, can be prepared by conventional peptide synthesis.

Detailed techniques to produce WGF by recombinant systems are known to those of skill in the art.

In Vitro and in Vivo Models

In vitro and in vivo models of acute renal failure are useful to study two major biological characteristics of wound repair: cell migration and proliferation. These models are suitable for analyzing the effects or the peptides of the present invention.

i. In vitro model: scrape-wounding of monolayer cultures of renal epithelial cells to simulate injured renal tubular epithelium.

In this model, high-density, quiescent monkey kidney epithelial monolayer cultures (BSC-1 line) are wounded by mechanically scraping away defined regions of the monolayer to simulate the effect of cell loss after tubular necrosis. The number of cells that migrate into the denuded area is counted (Kartha and Toback, 1992). It was found that cell migration is independent of cell proliferation, although both processes can be studied in this experimental preparation.

The model is useful to study the kinetics of renal epithelial cell migration, and identify genes whose expression is induced or repressed after wounding. The biological characteristics and potency of the WGF is suitable for investigations using this system.

ii. In vivo model: mercuric chloride (nephrotoxic) and renal clamping artery (ischemic) models of acute renal failure (ARF) in the rat.

Previous studies using this model system have characterized the clinical, histological, biochemical, and functional correlates of the acute renal failure syndrome. It was demonstrated that infusion of a mixture of essential and nonessential amino acids stimulates synthesis of phosphatidylcholine and protein in regenerating rat renal tissue and reduces the level of kidney dysfunction after intravenous administration of mercuric chloride (Toback, 1980). These studies showed that biochemical and functional repair of the injured kidney are not optimal in untreated animals and that provision of exogenous amino acids with glucose could speed recovery. The capacity of the WGF to enhance regeneration after acute renal failure is studied in this model.

It is important to define the onset of abnormal kidney function and structure, its course, and subsequent recovery. In humans, as is rats, kidney function during ARF is monitored by measurements of the concentration of serum creatinine and blood urea nitrogen (BUN) on a daily basis. These measurements provide estimates of glomerular filtration in the kidney which is one of its major functions. Creatinine enters the serum from muscle where it is released constantly as a consequence of the metabolic turnover of creatine phosphate, whereas the BUN is the end product of total body protein turnover. Both molecules make their way into the blood and because of their small size are excreted in the urine. Thus the extent to which they accumulate in the blood and are not excreted in ARF provides a guide to the extent of kidney injury.

Treatment of Chronic Renal Disease

The mechanisms that mediate the progression of renal disease in diabetic nephropathy, interstitial nephritis, and chronic glomerulonephritis are unknown. Relentless loss of renal function results in the need for chronic dialysis treatment at a cost of billions of dollars each year in the United States because at present there is no therapeutic strategy to slow or reverse the process. Patients early in the course of renal disease are suitable candidates for growth factor therapy because no other alternative is now available to treat this condition. The objective of administration of WGF is to speed recovery of injured renal epithelial cells along the nephron thereby repairing the damage mediated by the disease process, preserving renal function, and forestalling the need for dialysis.

Treatment of Renal Cell Cancer

Renal cell cancer is often a slow growing condition that results in widespread metastases to distant sites in the body making successful treatment difficult. Studies using radioactive WGF permit its receptor on renal cells to be identified and isolated; antibodies directed against the receptor are then prepared. These antibodies serve to localize receptors on specific types of kidney cells along the nephron. Armed with this information about the cell-type specificity of WGF receptors, strategies to treat cancers of renal cell types of interest include WGF or a specific WGF peptide that exhibits binding to the receptor and can thereby be used to deliver an anticancer agent to the proliferating cells of interest. Such anticancer agents comprise WGF or a specific WGF peptide or peptides conjugated to a toxin, cytolytic antibody, or a radioisotope. Although treatment of the primary renal tumor is likely best carried out by surgical extirpation of the organ, treatment of cancer metastases, especially those of small size, could be important targets of these novel chemotherapeutic agents that would be formulated using knowledge of WGF structure and function.

Delivery of WGF to Patients

Delivery to patients is generally by intravenous infusion similar to cancer chemotherapy deliveries or experimental treatment of small mammals. Another route is that used for treatment of anemia with erythropoietin (EPO) in renal failure wherein EPO is delivered every few days by subcutaneous injection.

Diagnosis of Renal Cell Injury by Use of an Antibody to WGF

The antibody to native WGF is prepared as disclosed herein and used to determine the concentration of the growth factor in urine and blood. Distribution of WGF in different types of renal cells along the nephron is determined. The concentration of the growth factor in either blood or urine or both could increase as a result of renal injury. If the growth factor is excreted in the urine as is epidermal growth factor, it may be possible to determine if renal injury leads to increased urinary excretion of the new factors. If so, enzyme-linked immunosorbent assay (ELISA) kits to detect WGF are used to rapidly diagnose early renal injury prior to a fall in glomerular filtration rate which is not detectable with conventional laboratory tests until more than 50% of kidney function is lost. This is particularly valuable in patients receiving drugs with nephrotoxic potential during treatment of severe infections or malignancies. An antibody to WGF is incorporated into a diagnostic ELISA kit designed to detect the appearance of growth factor in blood and urine of patients with renal injury or neoplasia.

Detection of Renal Cancer in Chronic Hemodialysis Patients

If renal adenomas, cystadenomas, or carcinomas that occur in remnant kidneys of patients undergoing chronic hemodialysis are found to overexpress the growth factor and excrete it in the urine, an ELISA kit could provide a new early detection system for these lesions. Such a diagnostic kit could also be used in asymptomatic but high-risk individuals. Renal cancer is now difficult to detect early because it tends to be asymptomatic until the tumor has grown to significant size or has metastasized widely.

Manipulations of Growth Factor, Structure and Functions

Analogs of the growth factor are developed to maximize the growth-promoting effect of WGF by optimizing specific binding to renal epithelial cell receptors. Inhibitors that block the biological action of each factor by binding to receptors on the cell surface are also useful. Development of a synthetic or recombinant product that is resistant to degradation would prolong pharmacological activity in vivo.

EXAMPLES

The following examples are provided for illustration, not limitation.

Example 1

14-Ser Peptide is Effective in the Treatment of Nephrotoxic Acute Renal Failure

Nephrotoxic and ischemic acute renal failure (ARF) induced experimentally in rats have long been used to model this syndrome in humans. To determine if the mitogenic effect of 14-Ser, a WGF-derived $NH_2$-terminal peptide, would prove efficacious as a therapeutic agent in animals with ARF, acute tubular necrosis was induced by injecting a solution of mercuric chloride (in normal saline) subcutaneously to rats at a dose of 2.25 mg per kilogram body weight. Male rats weighed 200–225 gm at the start of the experiment. This dose was used because preliminary experiments indicated it results in survival of 25–50% of the animals 7 days later. Blood was obtained from the tail vein each day and the concentration of creatinine in the serum was measured and used as an index of renal function. An increase in serum creatinine concentration signals a decline in renal function because the injured kidney is unable to excrete endogenous creatinine in the urine so it accumulates in the blood.

The synthetic peptide AQPYPQGNHEASYG (14-Ser) (SEQ ID NO: 15) (dissolved in sterile 0.01% bovine serum albumin in phosphate-buffered saline) was injected subcutaneously into rats to determine its effect on survival, recovery of renal function, and stimulation of DNA synthesis. Multiple different peptides were studied including 14-Ser, AQPYPEGNHEASYG (14-mer) (SEQ ID NO: 39), AQPYPQGNHEATSSSF (16-mer) (SEQ ID NO: 4) AQPYPQGNHEA (11-mer) (SEQ ID NO: 6), and AQPYPEGNHEA (11-mer) (SEQ ID NO: 41). Different concentrations and times of administration were tested and compared. The results indicated that 14-Ser was the most effective WGF-derived peptide; it improved survival and recovery of renal function, and stimulated DNA synthesis in the regenerating kidney after mercuric chloride-induced ARF.

Acute tubular necrosis was induced in 44 rats by the subcutaneous (s.c.) injection of mercuric chloride, and a single dose of 14-ser was administered s.c. 1 hour afterwards. Different amounts of the peptide were given to assesses its capacity to affect the outcome. Survival 7 days later was about twice as high in animals given 100–150 µg of peptide (63%) than in rats given 0–75 µg peptide (29%).

Figure 2A:
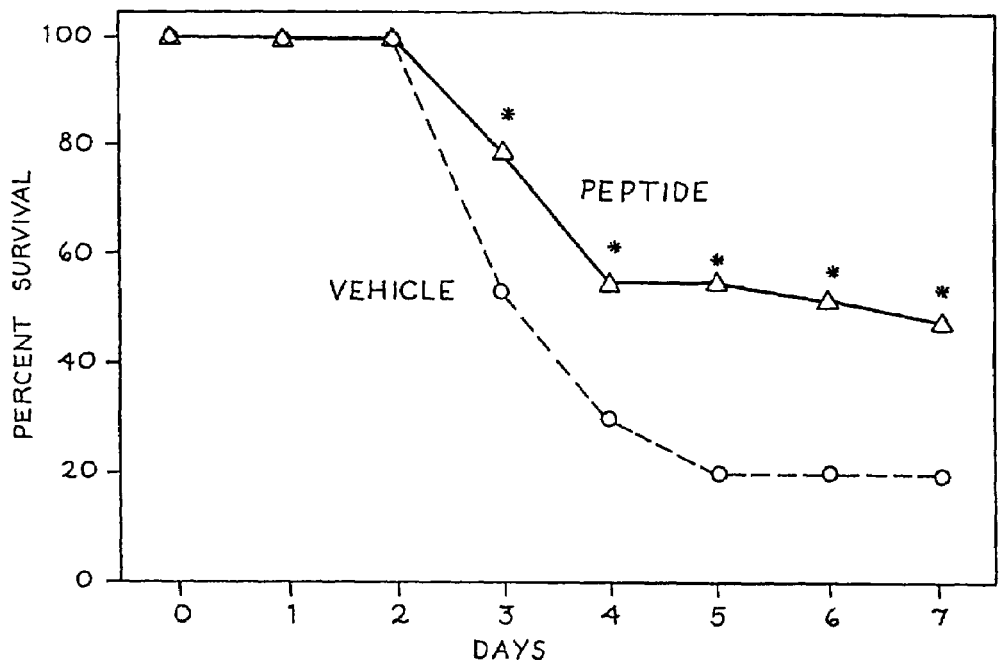
FIG. 2 illustrates enhanced survival (FIG. 2A) and renal functional recovery (FIG. 2B) of rats given a WGF-derived peptide (14 Ser) after mercuric chloride-induced acute tubular necorsis.
(FIG. 2B: Values are means±standard error. *, Student's t-test, p<0.034) (FIG. 2A: Percent survival is number of rats alive divided by total number alive and dead; *, chi squared, P<0.050.)
Figure 2B:
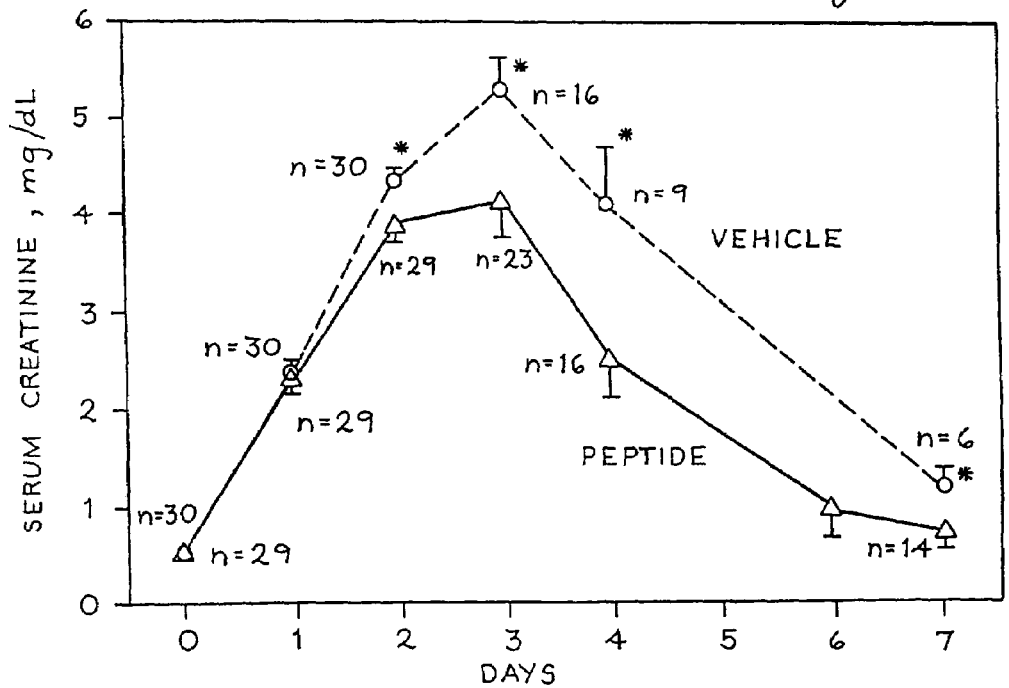

To determine the effect of the peptide on survival and recovery of renal function, acute tubular necrosis was induced in 59 rats; 29 received 14-Ser (100 µg/rat) and 30 received an equal volume of the vehicle s.c. 1 hour after administration of mercuric chloride. Enhanced survival (top panel) and renal functional recovery (bottom panel) of rats give a WGF-derived peptide after mercuric chloride-induced acute tubular necrosis are shown in FIG. 2A and FIG. 2B. Mercuric chloride was injected subcutaneously into each of the 59 rats, and 1 hour later 100 µg of WGF peptide (14-Ser) (n=29 rats) or the vehicle (n=3–) was given. Survival was greater in rats given the peptide than in animals receiving the vehicle as early as day 3 after administration of mercuric chloride. Blood was obtained from the tail vein on the days indicated, and serum creatinine concentration was measured. A similar increase in creatinine concentration was observed in both groups of animals on day 1, signifying that they sustained the same extent of renal functional injury. On days 2, 3 and 4, the lower creatinine concentration in peptide-treated rats indicates accelerated recovery of kidney function.

FIG. 2A indicates that the survival of rats given the peptide was significantly greater (chi squared, $P=0.035$) than those given vehicle 3 days after the onset of the ARF syndrome, a difference that persisted during the next 4 days. By day 7 only 20% of rats that received the vehicle were alive, whereas 48% of rats given the peptide survived (chi squared, $P=0.012$).

Assessment of renal function during the onset of the ARF syndrome revealed impaired function on the day 1 when the creatinine concentration increased from the basal value of 0.5 mg/dL to 2.3 mg/dL. It was similar in animals treated with the peptide (n-29 rats) or the vehicle alone (n=30) (FIG. 2B), suggesting that the extent of renal injury was equivalent in both peptide-treated and untreated animals. On day 2 the serum creatinine concentration was significantly lower in peptide-treated rats (n=29) than in animals given the vehicle (n=30) ($P=0.034$, Student's t-test), indicating that the decline in renal function was less severe in rats given mercuric chloride followed by the peptide. Evidence of a significantly more rapid recovery of renal function was also apparent on days 3 and 4 after the onset of ARF. Similar beneficial effect of the peptide administration was observed when the blood urea nitrogen concentration was measured as an index of renal function. These results indicate that a WGF peptide that is mitogenic for renal epithelial cells can speed renal functional recovery and enhance survival of rats with nephrotixic ARF.

In a separate set of experiments, 14-Ser (n=7) or vehicle (n=9) was given to rats 24 hours before mercuric chloride-induced injury. On day 3, renal function assessed using the serum creatinine concentration was significantly better in rats given the peptide ($P=0.039$). Survival on day 4 was 71% in rats treated with the peptide but only 22% in those given the vehicle (chi squared, $P=0.049$). Treatment with the 14-Ser peptide 24 hours before the mercuric chloride-induced insult appeared to have a more favorable effect on survival than when given 1 hour afterwards, although the difference did not quite achieve statistical significance.

To determine if the beneficial effects of 14-Ser peptide on survival and renal function were the result of the mitogenic action of the peptide, DNA synthesis was measured in the kidneys of rats given mercuric chloride. 5-Bromo-2'-deoxyuridine (BrdU), a nonradioactive analog of thymidine that is incorporated into DNA was used to label nuclei. A monoclonal antibody to BrdU and diamidobenzidene staining were used to detect nuclei undergoing DNA synthesis in histological sections of renal tissue. BrdU was dissolved in 20% ethanol and was injected intra-peritoneally 23 hours after administration of mercuric chloride. One hour later the kidneys were quickly perfused with a warm solution of phosphate-buffered saline via an aortic catheter to eliminate red blood cells from the organ and maintain potency of the renal tubules. The capsule was removed from the kidneys which were the bisected longitudinally, and fixed in formalin for 4 hours, and then in 70% ethanol. Tissue sections were prepared and BrdU-labeled nuclei were detected as described above.

BrdU staining of kidneys of rats given no mercuric chloride revealed about 3 labeled nuclei per high-power field (X400) in the subcapsular and aglomerular (inner) cortex. In the kidneys of a rats given mercuric chloride, extensive necrosis of tubular cells of the terminal portion ($S_3$) of the proximal nephron was observed, as expected in this well-characterized model system. The extent of necrosis was somewhat variable from rat-to-rat but was always confined to the aglomerular cortex. Fewer labeled cells were seen in the aglomerular cortex in rats given mercuric chloride 24 hours earlier than in cells of untreated control rats. Renal tissue from a rat given 14-Ser (100 µg) 24 hours before administration of mercuric chloride was also examined. In this animal, 1 hour of BrdU labeling was carried out 24 hours after mercuric chloride as described herein. Microscopic examination revealed that many more labeled nuclei were present adjacent to the zone of tubular cell necrosis. This finding is important because it is in this boundary area of the cortex where regenerating cells are expected to undergo mitosis and then migrate into nephrons in the necrotic zone to replace cells that were irreversibly injured by the nephrotoxic insult. Thus the 14-Ser peptide appears to stimulate DNA synthesis in cells of regenerating nephrons after mercuric chloride-induced tubular necrosis, and could thereby speed recovery of renal function and improve survival after ARF.

Example 2

Improved Survival with 11-mer WGF-Derived Peptide Treatment of Experimental Acute Renal Failure Experimental ARF was induced in rats by subcutaneous injection of mercuric chloride. The synthetic peptide AQPYPEGNHEA (SEQ ID NO: 41) (dissolved in sterile 0.01% bovine serum albumin and PBS) was injected subcutaneously into rats two hours after mercuric chloride was given to demonstrate its beneficial effect on survival from the ARF syndrome. In one experiment a total of 17 rats were injected with a dose of mercuric chloride shown to induce ARF. The different amounts of the peptide (known to stimulate growth of kidney cells in culture) were injected into the animals to assess capacity to improve the outcome. Three days later, five of five animals given saline alone and three of three rats given 50 micrograms of the peptide were dead. In contrast, two of three rats given 100 micrograms of peptide were alive, as were five of six given 200 micrograms. In summary, none of eight rats (0%) given up to 50 micrograms of peptide survived, whereas seven of nine (78%) given 100–200 micrograms did. Thus, the 1'-mer WGF peptide improves survival in nephrotoxic ARF.

Example 3

Effect of Specific WGF-Derived Peptides on Kidney Repair

In addition, administration of specific WGF-derived peptides or the native protein speeds repair of renal structure. Standard assays in renal growth physiology and pathology are used to demonstrate that the growth-promoting (mitogenic) effect of a WGF peptide or the 22 or 45 kDa protein stimulates an increased number of kidney cells to initiate synthesis of DNA in preparation for cell division, as has been shown in tissue culture.

Initially, sections of kidney tissue from rats with mercuric chloride-induced ARF are prepared and inspected under light microscopy to compare the extent of renal injury and repair in animals that received WGF peptide and those that received a saline vehicle alone. Another measure of the effect of WGF on recovery is an histopathological assessment based on detailed microscopic inspection of kidney tissue. A scoring system that grades the characteristic features of ARF and recovery is used to assess and compare kidney tissue from rats that did or did not receive treatment with WGF. (Miller et al., 1994).

Depending upon methodologic considerations, radioactive thymidine can be used to measure the capacity of WGF protein or peptide to stimulate renal DNA synthesis after ARF. In these experiments radioactive thymidine is injected intraperitoneally 1 hour before death, and its incorporation into renal DNA is determined by subsequently extracting DNA from the tissue, and then measuring the amount of DNA by a chemical assay, and its radioactivity by scintillation counting. Autoradiogrms can also be prepared and used to determine which cells in kidney tissue have incorporated radioactive thymidine into DNA. All the techniques referred to are known in the art.

An ischemic model of ARF is also suitable. In these rats, pentobarbital anesthesia is induced and the kidneys are deprived of blood flow for 60 minutes by placing surgical clamps on each renal pedicle (artery, vein, ureter) that is first exposed at surgery. This is an established model of ARF. After the clamps are released to restore blood flow to the kidneys, the surgical incision sites in the skin and muscle are closed with skin clips, and the animals are treated with WGF peptide by injection s.c. Measurements of recovery of renal function and structure are the same as for the toxic (mercuric chloride) model described herein.

Example 4

Inhibition of WGF-Derived Peptide Mitogenesis by TGF-$\beta$2 and YPQGN (SEQ ID NO: 3) Peptide To better understand the role of the 14-Ser peptide in renal cell growth regulation, agents that could inhibit its mitogenic effect were studied.

Transforming growth factor (TGF)-$\beta$2 is an autocrine growth inhibitor secreted by BSC-1 cells that limits proliferation in culture. Exogenous TGF-$\beta$2 was added to the culture medium to determine its capacity to inhibit the growth-promoting effect of 14-Ser. TGF-$\beta$2 at a concentration of 1 ng/ml was sufficient to abolish the 25% stimulation of growth induced by 14-Ser. At a TGF-$\beta$2 concentration of 2 ng/ml, growth was inhibited by 30% in the presence or absence of 14-Ser; at 10 ng/ml, inhibition was 60%. At a TGF-$\beta$2 concentration of 6 ng/ml, exogenous 14-Ser up to 5 $\mu$g/ml did not reverse growth inhibition.

Because TGF-$\beta$2 inhibits proliferation induced by diverse mitogens, a more specific inhibitor was sought. Previously, studies of the 5-amino acid WGF-derived peptides YPQGN (SEQ ID NO: 3) and PQGNH (SEQ ID NO: 36) were shown to inhibit the mitogenic effect of the 6-amino acid peptide, YPQGNH (SEQ ID NO: 2). These pentapeptides do not alter growth when added to cells. Cells were preincubated for 30 minutes with the pentapeptide YPQGN (SEQ ID NO: 3). The culture medium was then aspirated, the monolayer was rinsed, fresh medium was added, and the number of cells counted 4 days later. Preincubation of cells with YPQGN (SEQ ID NO: 3) inhibited the mitogenic effect of the 6-amino acid peptide. In addition, preincubation with YPQGN (SEQ ID NO: 3) for 10 or 30 minutes completely blocked the growth-promoting effect of the 14-Ser peptide as well. Importantly, the mitogenic effect of partially-purified Wound Growth Factor (passed over an heparin-affinity cartridge, not an HPLC column) was also completely abolished.

These observations suggest that the 14-Ser and YPQGNH (SEQ ID NO: 2) (WGF-derived) peptides, and partially-purified WGF bind to the sane cell surface receptor, which also has a high affinity for the pentapeptide YPQGN (SEQ ID NO: 3). The WGF receptor may be isolated and characterized using high affinity ligands such as the 14-Ser peptide and the 40-amino acid peptide which can readily be radio-iodinated for use as probes.

Example 5

Comparison Between the 14-Ser WGF-Derived Peptide and EGF on Survival After Acute Renal Failure The efficacy of the 14-Ser peptide as a novel therapeutic agent in mercuric chloride-induced ARF was compared to EGF, which was the first peptide growth factor shown to be effective in this animal model system.

Either rats in each of three groups (N=24) were given either 14-Ser (100 μg, s.c.) 1 hour after mercuric chloride (2.25 mg/kg s.c.), EGF (20 μg, s.c.) 2 hours after the toxin, or the vehicle (s.c.), and survival was monitored. Four days later, 63% of rats given the 14-Ser peptide were alive compared to 25% of animals receiving the vehicle (chi squared, P–0.0499); 50% of rats receiving EGF were alive (chi squared, P=N.S.). On day 5, 50% of rats given EGF were alive, compared to 12.5% of animals given the vehicle (chi squared, P=0.0436). On day 6, survival was identical in rats given the 14-Ser peptide or EGF (37.5%) compared to 12% of animals treated with the vehicle. These observations indicate that the 14-Ser peptide and EGF given after renal injury are similar in their ability to improve survival from the ARF syndrome.

In a separate experiment, rats were given EGF (20 μg, s.c.) 24 hours prior to administration of mercuric chloride to compare the effect of this growth factor to the 14-Ser peptide. Surprisingly, EGF treatment was not different than the vehicle, whereas the 14-Ser peptide is highly protective under these conditions. Thus, on day 4, survival of rats given EGF was 25%, for vehicle, 31%, and for the 14-Ser WGF-derived peptide, 73%.

These studies indicate that the 14-Ser peptide is more effective than EGF in promoting survival when administered prophylactically, i.e., before the onset of renal injury. Administration of WGF-derived peptide could prove particularly efficacious: (1) prior to surgical procedures in patients with a high risk of developing ARF (e.g., the elderly, neonates), (2) in patients given potentially nephrotoxic agents such as antibiotics for treatment of sepsis or antineoplastic agents, and (3) for perfusion of donor kidneys prior to their transplantation into new hosts.

Documents Cited

Broccardo, M., Falconieri Erspamer G., Melchiorri P., Negri, L., and De Castiglione, R., "Relative potency of bombesin-like peptides," *Journal of Pharmacology* 55: 221–227 (1975).

Coimbra T. M., Cieslinski, D. A., and Humes, H. D. "Epidermal growth factor accelerates renal repair in mercuric chloride nephrotoxicity," *American Journal of Physiology* 259: F438–F443, 1990.

Heimbrook, D. C., Boyer, M. E., Garsky, V. M., Balishin, N. L., Kiefer, D. M., Oliff, A., and Rieman, M. W., "Minimal ligand analysis of gastrin releasing peptide. Receptor binding and mitogenesis," *Journal of Biological Chemistry* 263: 7016–7019 (1988).

Kartha, S., and Toback, F. G., "Adenine nucleotides stimulate migration in wounded cultures of kidney epithelial cells," *Journal of Clinical Investigation*, 90: 288–292 (1992).

Kartha, S., and Toback, F. G. "Purine nucleotides stimulate DNA synthesis in idney epithelial cells in culture," American Journal of Physiology 249: F967–F972, 1985.

Levy, E. M., Viscoli, C. M. and Horowitz, R. I. The Effect of Acute Renal Failure on Mortality, "A Cohort Analysis," *Journal of the American Medical Association*, 275: 1489–1494 (1996).

Mendley, S. R., and Toback, F. G., "Autocrine and paracrine regulation of kidney epithelial cell growth," *Annual Review of Physiology*, 51: 33–50 (1989).

Miller, S. B., Martin, D. R., Kissane, J. and Hammerman, M. R. "Hepatocyte growth factor accelerates recovery from acute ischemic renal injury in rats." *American Journal of Physiology* 266: F129–F134 (1994).

Mordan, L. J., and Toback, "Growth of kidney epithelial cells in culture: Evidence for autocrine control," *American Journal of Physiology*, 246: C351–C354 (1984).

National Center for Health Statistics, National Institute of Health, 1995.

National Kidney and Urological Advisory Board, 1990 Long Range Plan.

Toback, F. G., "Amino acid treatment of acute renal failure," In Contemporary Issues in Nephrology, ed. Brenner, B. M. and Stein, J. H. Vol. 6, pp. 202–228, Churchill Livingstone, N.Y. (1980).

Toback, F. G., "Control of renal regeneration after acute tubular necrosis," *Nephrology*, Proceedings IXth International Congress of Nephrology, I: 748–762 (1984).

Toback, F. G., "Induction of growth in kidney cells in culture by $Na^+$," *Proceedings of the National Academy of Sciences, USA*, 77: 6654–6656, 1980.

Toback, F. G., "Regeneration after acute tubular necrosis," *Kidney International*, 41: 226–246 (1992).

Toback, F. G., Ekelman, K. B., and Ordonez, N. G. "Stimulation of DNA synthesis in kidney epithelial cells in culture by potassium," *American Journal of Physiology* 247: C14–C19, 1984.

Toback, et al., U.S. Pat. No. 5,135,856, issued Aug. 4, 1992 (b) and U.S. Pat. No. 5,476,922, issued Dec. 19, 1995.

Walsh-Reitz, M. M., Gluck, S. L., Waack, S. and Toback, F. G., "Lowering extracellular $Na^+$ concentration releases autocrine growth factors from renal epithelial cells," *Proceedings of the National Academy of Sciences, USA*, 83: 4764–4768 (1986).

Walsh-Reitz, M. M. and Toback, F. G. "Vasopressin stimulates growth of renal epithelial cells in culture." *American Journal of Physiology* 245: C365–370, 1983.

We claim:

1. A method of treating a mammal with acute renal failure, said method comprising:
   (a) preparing a preparation comprising a pharmacologically effective amount of a native wound growth factor (WGF) protein comprising an amino acid sequence of SEO ID NO: 2 in a suitable diluent; and
   (b) administering the preparation to the mammal.

2. The method of claim 1, wherein the mammal is a human.

3. A method of treating a mammal with acute renal failure, said method comprising:
   (a) preparing a preparation comprising a pharmacologically effective amount of a peptide derived from a wound growth factor (WGF) protein, wherein the WGF-derived peptide comprises a sequence selected from the group consisting of:
AQPYPQGNHEATSSSF (SEQ ID NO: 4);
AQPYPQGNHEATSSS (SEQ ID NO: 5);
AQPYPQGNHEA (SEQ ID NO: 6);
AQPYPQGNHEAT (SEQ ID NO: 7);
AQPYPQGNHEATS (SEQ ID NO: 8);
AQPYPQGNHEATSS (SEQ ID NO: 9);
AQPYPQGNHEATSY (SEQ ID NO: 10);
AQPYPQGNHEMYG (SEQ ID NO: 11);
AQPYPQGNHEMY (SEQ ID NO: 12);
AQPYPQGNHEM (SEQ ID NO: 13);
AQPYPQGNHE (SEQ ID NO: 14);
AQPYPQGNHEASYG (SEQ ID NO: 15);
AQPYPQGNHEASY (SEQ ID NO: 16);
AQPYPQGNHEAS (SEQ ID NO: 17);
QPYPQGNHEA (SEQ ID NO: 18);
AQPYPQGNH (SEQ ID NO: 19;
QPYPQGNHE (SEQ ID NO: 20);
PYPQGNHEA (SEQ ID NO: 21);
QPYPQGNH (SEQ ID NO: 22);
PYPQGNHE (SEQ ID NO: 23);
YPQGNHEA (SEQ ID NO: 24);
PYPQGNH (SEQ ID NO: 25);
YPQGNHE (SEQ ID NO: 26);
YPQGNHEATSSSF (SEQ ID NO: 27);
YPQGNHEATSSS (SEQ ID NO: 28);
YPQGNHEATSS (SEQ ID NO: 29);
YPQGNHEATS (SEQ ID NO: 30); and
YPQGNHEAT (SEQ ID NO: 31); and
   (b) administering the preparation to the mammal.

4. The method of claim 3, wherein the mammal is a human.

* * * * *

SEQUENCE LISTING (1) GENERAL INFORMATION:

(iii) NUMBER OF SEQUENCES: 49

```
(2) INFORMATION FOR SEQ ID NO: 1:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (ix) FEATURE:
         (A) NAME/KEY: Modified-site
         (B) LOCATION: 11
         (D) OTHER INFORMATION: /product= "Unknown"

(ix) FEATURE:
         (A) NAME/KEY: Modified-site
         (B) LOCATION: 12
         (D) OTHER INFORMATION: /product= "Ala or Ser"

(xi) SEQUENCE DESCRIPTION: SEQ ID NO: 1:

Ala Gln Pro Tyr Pro Gln Gly Asn His Glu Xaa Xaa Tyr Gly
1               5                   10

(2) INFORMATION FOR SEQ ID NO: 2:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 2:

Tyr Pro Gln Gly Asn His
1               5

(2) INFORMATION FOR SEQ ID NO: 3:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 3:

Tyr Pro Gln Gly Asn
1               5

(2) INFORMATION FOR SEQ ID NO: 4:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 4:

Ala Gln Pro Tyr Pro Gln Gly Asn His Glu Ala Thr Ser Ser Ser Phe
1               5                   10                  15

(2) INFORMATION FOR SEQ ID NO: 5:

(i) SEQUENCE CHARACTERISTICS:
        (A) LENGTH: 15 amino acids
        (B) TYPE: amino acid
```

```
            (C) STRANDEDNESS: <Unknown>
            (D) TOPOLOGY: linear (ii) MOLECULE TYPE: peptide (xi) SEQUENCE DESCRIPTION: SEQ ID NO: 5:

Ala Gln Pro Tyr Pro Gln Gly Asn His Glu Ala Thr Ser Ser Ser
1               5                  10                  15

(2) INFORMATION FOR SEQ ID NO: 6:

(i) SEQUENCE CHARACTERISTICS:
            (A) LENGTH: 11 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 6:

Ala Gln Pro Tyr Pro Gln Gly Asn His Glu Ala
1               5                  10

(2) INFORMATION FOR SEQ ID NO: 7:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 7:

Ala Gln Pro Tyr Pro Gln Gly Asn His Glu Ala Thr
1               5                  10

(2) INFORMATION FOR SEQ ID NO: 8:

(i) SEQUENCE CHARACTERISTICS:
            (A) LENGTH: 13 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 8:

Ala Gln Pro Tyr Pro Gln Gly Asn His Glu Ala Thr Ser
1               5                  10

(2) INFORMATION FOR SEQ ID NO: 9:

(i) SEQUENCE CHARACTERISTICS:
            (A) LENGTH: 14 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 9:

Ala Gln Pro Tyr Pro Gln Gly Asn His Glu Ala Thr Ser Ser
1               5                  10

(2) INFORMATION FOR SEQ ID NO: 10:

(i) SEQUENCE CHARACTERISTICS:
            (A) LENGTH: 14 amino acids
```

```
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 10:

Ala Gln Pro Tyr Pro Gln Gly Asn His Glu Ala Thr Ser Tyr
1               5                   10

(2) INFORMATION FOR SEQ ID NO: 11:

(i) SEQUENCE CHARACTERISTICS:
            (A) LENGTH: 14 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 11:

Ala Gln Pro Tyr Pro Gln Gly Asn His Glu Ala Ala Tyr Gly
1               5                   10

(2) INFORMATION FOR SEQ ID NO: 12:

(i) SEQUENCE CHARACTERISTICS:
            (A) LENGTH: 13 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 12:

Ala Gln Pro Tyr Pro Gln Gly Asn His Glu Ala Ala Tyr
1               5                   10

(2) INFORMATION FOR SEQ ID NO: 13:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 13:

Ala Gln Pro Tyr Pro Gln Gly Asn His Glu Ala Ala
1               5                   10

(2) INFORMATION FOR SEQ ID NO: 14:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 14:

Ala Gln Pro Tyr Pro Gln Gly Asn His Glu
1               5                   10

(2) INFORMATION FOR SEQ ID NO: 15:

(i) SEQUENCE CHARACTERISTICS:
```

(A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 15:

Ala Gln Pro Tyr Pro Gln Gly Asn His Glu Ala Ser Tyr Gly
1               5                   10

(2) INFORMATION FOR SEQ ID NO: 16:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 16:

Ala Gln Pro Tyr Pro Gln Gly Asn His Glu Ala Ser Tyr
1               5                   10

(2) INFORMATION FOR SEQ ID NO: 17:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 17:

Ala Gln Pro Tyr Pro Gln Gly Asn His Glu Ala Ser
1               5                   10

(2) INFORMATION FOR SEQ ID NO: 18:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 18:

Gln Pro Tyr Pro Gln Gly Asn His Glu Ala
1               5                   10

(2) INFORMATION FOR SEQ ID NO: 19:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 19:

Ala Gln Pro Tyr Pro Gln Gly Asn His
1               5

(2) INFORMATION FOR SEQ ID NO: 20:

(i) SEQUENCE CHARACTERISTICS:
            (A) LENGTH: 9 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 20:

Gln Pro Tyr Pro Gln Gly Asn His Glu
1               5

(2) INFORMATION FOR SEQ ID NO: 21:

(i) SEQUENCE CHARACTERISTICS:
            (A) LENGTH: 9 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 21:

Pro Tyr Pro Gln Gly Asn His Glu Ala
1               5

(2) INFORMATION FOR SEQ ID NO: 22:

(i) SEQUENCE CHARACTERISTICS:
            (A) LENGTH: 8 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 22:

Gln Pro Tyr Pro Gln Gly Asn His
1               5

(2) INFORMATION FOR SEQ ID NO: 23:

(i) SEQUENCE CHARACTERISTICS:
            (A) LENGTH: 8 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 23:

Pro Tyr Pro Gln Gly Asn His Glu
1               5

(2) INFORMATION FOR SEQ ID NO: 24:

(i) SEQUENCE CHARACTERISTICS:
            (A) LENGTH: 8 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 24:

Tyr Pro Gln Gly Asn His Glu Ala
1               5

(2) INFORMATION FOR SEQ ID NO: 25:

```
    (i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 25:

Pro Tyr Pro Gln Gly Asn His
1               5

(2) INFORMATION FOR SEQ ID NO: 26:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 26:

Tyr Pro Gln Gly Asn His Glu
1               5

(2) INFORMATION FOR SEQ ID NO: 27:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 27:

Tyr Pro Gln Gly Asn His Glu Ala Thr Ser Ser Ser Phe
1               5                   10

(2) INFORMATION FOR SEQ ID NO: 28:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 28:

Tyr Pro Gln Gly Asn His Glu Ala Thr Ser Ser Ser
1               5                   10

(2) INFORMATION FOR SEQ ID NO: 29:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 29:

Tyr Pro Gln Gly Asn His Glu Ala Thr Ser Ser
1               5                   10
```

(2) INFORMATION FOR SEQ ID NO: 30:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 30:

Tyr Pro Gln Gly Asn His Glu Ala Thr Ser
1               5                   10

(2) INFORMATION FOR SEQ ID NO: 31:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 31:

Tyr Pro Gln Gly Asn His Glu Ala Thr
1               5

(2) INFORMATION FOR SEQ ID NO: 32:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 14
        (D) OTHER INFORMATION: /product= "Ser or Tyr"

(xi) SEQUENCE DESCRIPTION: SEQ ID NO: 32:

Ala Gln Pro Tyr Pro Gln Gly Asn His Glu Ala Thr Ser Xaa
1               5                   10

(2) INFORMATION FOR SEQ ID NO: 33:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 33:

Tyr Pro Glu Gly Asn His
1               5

(2) INFORMATION FOR SEQ ID NO: 34:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 34:

Gln Pro Tyr Pro Gln Gly
1               5

(2) INFORMATION FOR SEQ ID NO: 35:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 35:

Gly Asn His Glu
1

(2) INFORMATION FOR SEQ ID NO: 36:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 36:

Pro Gln Gly Asn His
1               5

(2) INFORMATION FOR SEQ ID NO: 37:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 37:

Tyr Pro Arg Gly Asn His
1               5

(2) INFORMATION FOR SEQ ID NO: 38:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 38:

Leu Lys Tyr Ser Gly Gln Asp
1               5

(2) INFORMATION FOR SEQ ID NO: 39:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 39:

Ala Gln Pro Tyr Pro Glu Gly Asn His Glu Ala Ser Tyr Gly
1               5                   10

(2) INFORMATION FOR SEQ ID NO: 40:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 40:

Tyr Pro Gln Gly Asn His Glu Ala Ser Tyr Gly
1               5                   10

(2) INFORMATION FOR SEQ ID NO: 41:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 41:

Ala Gln Pro Tyr Pro Glu Gly Asn His Glu Ala
1               5                   10

(2) INFORMATION FOR SEQ ID NO: 42:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 42:

Tyr Pro Glu Gly Asp His
1               5

(2) INFORMATION FOR SEQ ID NO: 43:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 43:

Tyr Pro Glu Gly Lys His
1               5

(2) INFORMATION FOR SEQ ID NO: 44:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 44:

Phe Pro Glu Gly Asn His
1               5

(2) INFORMATION FOR SEQ ID NO: 45:

(i) SEQUENCE CHARACTERISTICS:
        (A) LENGTH: 27 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 45:

Val Pro Leu Pro Ala Gly Gly Thr Val Leu Thr Lys Met Tyr Pro
1               5                   10                  15

Arg Gly Asn His Trp Ala Val Gly His Leu Met
            20                  25

(2) INFORMATION FOR SEQ ID NO: 46:

(i) SEQUENCE CHARACTERISTICS:
        (A) LENGTH: 27 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 46:

Ala Pro Val Ser Val Gly Gly Thr Val Leu Ala Lys Met Tyr Pro
1               5                   10                  15

Arg Gly Asn His Trp Ala Val Gly His Leu Met
            20                  25

(2) INFORMATION FOR SEQ ID NO: 47:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 47:

Glu Gln Arg Leu Gly Asn Gln Trp Ala Val Gly His Leu Met
1               5                   10

(2) INFORMATION FOR SEQ ID NO: 48:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 48:

Trp Ala Val Gly His Leu Met
1               5

(2) INFORMATION FOR SEQ ID NO: 49:

```
    (i) SEQUENCE CHARACTERISTICS:
        (A) LENGTH: 40 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 49:

Ala Gln Pro Tyr Pro Gln Gly Asn His Glu Ala Gln Pro Tyr Pro Gln
1               5                  10                  15

Gly Asn His Glu Ala Gln Pro Tyr Pro Gln Gly Asn His Glu Ala Gln
            20                  25                  30

Pro Tyr Pro Gln Gly Asn His Glu
        35                  40
```